US012178505B2

(12) United States Patent
Hancock et al.

(10) Patent No.: US 12,178,505 B2
(45) Date of Patent: Dec. 31, 2024

(54) MODULAR ELECTROSURGICAL SYSTEM, AND MODULES FOR SAID SYSTEM

(71) Applicant: CREO MEDICAL LIMITED, Monmouth (GB)

(72) Inventors: Christopher Paul Hancock, Chepstow (GB); George Hodgkins, Chepstow (GB); John Bishop, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 746 days.

(21) Appl. No.: 17/298,249

(22) PCT Filed: Nov. 26, 2019

(86) PCT No.: PCT/EP2019/082571
§ 371 (c)(1),
(2) Date: May 28, 2021

(87) PCT Pub. No.: WO2020/120125
PCT Pub. Date: Jun. 18, 2020

(65) Prior Publication Data
US 2022/0117660 A1 Apr. 21, 2022

(30) Foreign Application Priority Data
Dec. 10, 2018 (GB) .................................... 1820060

(51) Int. Cl.
*A61B 18/18* (2006.01)
*A61B 17/00* (2006.01)
(Continued)

(52) U.S. Cl.
CPC ........ *A61B 18/1815* (2013.01); *A61B 18/042* (2013.01); *A61B 18/14* (2013.01);
(Continued)

(58) Field of Classification Search
CPC .............. A61B 18/1815; A61B 18/042; A61B 2017/00221; A61B 2018/00928;
(Continued)

(56) References Cited

U.S. PATENT DOCUMENTS

2005/0251228 A1 11/2005 Hamel
2010/0049031 A1* 2/2010 Fruland .................. A61B 18/16
600/439
(Continued)

FOREIGN PATENT DOCUMENTS

CN 103347455 A 10/2013
EP 1498082 A1 1/2005
(Continued)

OTHER PUBLICATIONS

International Preliminary Report on Patentability issued from the International Preliminary Examining Authority in counterpart International Application No. PCT/EP2019/082571, mailed on Feb. 22, 2021.
(Continued)

*Primary Examiner* — Joseph A Stoklosa
*Assistant Examiner* — Annie L Shoulders
(74) *Attorney, Agent, or Firm* — ArentFox Schiff LLP

(57) ABSTRACT

The invention relates to a modular electrosurgical system for using electromagnetic (EM) radiation, such as radio frequency (RF) or microwave EM radiation, to treat biological tissue. In one example, control of the modules is centralised in a remote computing device which can communicate wirelessly with the modules of the system. In one example, different optional modules may be combined together with core modules to provide the system with different electrosurgical capabilities.

24 Claims, 9 Drawing Sheets

(51) Int. Cl.
 *A61B 18/04* (2006.01)
 *A61B 18/14* (2006.01)
 *A61B 18/00* (2006.01)

(52) U.S. Cl.
 CPC .............. *A61B 2017/00221* (2013.01); *A61B 2018/00577* (2013.01); *A61B 2018/00601* (2013.01); *A61B 2018/00714* (2013.01); *A61B 2018/00732* (2013.01); *A61B 2018/00744* (2013.01); *A61B 2018/00755* (2013.01); *A61B 2018/00898* (2013.01)

(58) Field of Classification Search
 CPC ............ A61B 2560/0443; A61B 18/18; A61B 2018/1823; A61B 2018/00898
 See application file for complete search history.

(56) References Cited

U.S. PATENT DOCUMENTS

| | | | | |
|---|---|---|---|---|
| 2013/0267943 | A1* | 10/2013 | Hancock | H05B 6/806 606/33 |
| 2014/0276771 | A1* | 9/2014 | Miller | A61B 18/1233 606/34 |
| 2015/0257817 | A1* | 9/2015 | Zoran | A61B 18/1402 606/45 |
| 2016/0310204 | A1* | 10/2016 | McHenry | A61B 18/1233 |
| 2019/0008580 | A1* | 1/2019 | Fischell | A61B 17/2202 |
| 2019/0274752 | A1* | 9/2019 | Denzinger | A61B 18/1445 |
| 2019/0343591 | A1* | 11/2019 | Raz | A61B 5/113 |

FOREIGN PATENT DOCUMENTS

| | | |
|---|---|---|
| EP | 3 087 942 A1 | 11/2016 |
| JP | 2017-225818 A | 12/2017 |

OTHER PUBLICATIONS

International Search Report and Written Opinion, issued by International Searching Authority in corresponding International Application No. PCT/EP2019/082571, mailed on Jun. 25, 2020.

Search Report under Section 17(6), issued by the United Kingdom Intellectual Property Office in counterpart United Kingdom Application No. GB1820060.0, dated Jun. 28, 2019.

Search Report under Section 17(5), issued by the United Kingdom Intellectual Property Office in counterpart United Kingdom Application No. GB1820060.0, dated May 21, 2019.

Written Opinion of the International Preliminary Examining Authority, issued by the International Preliminary Examining Authority in corresponding International Application No. PCT/EP2019/082571, mailed on Nov. 17, 2020.

\* cited by examiner

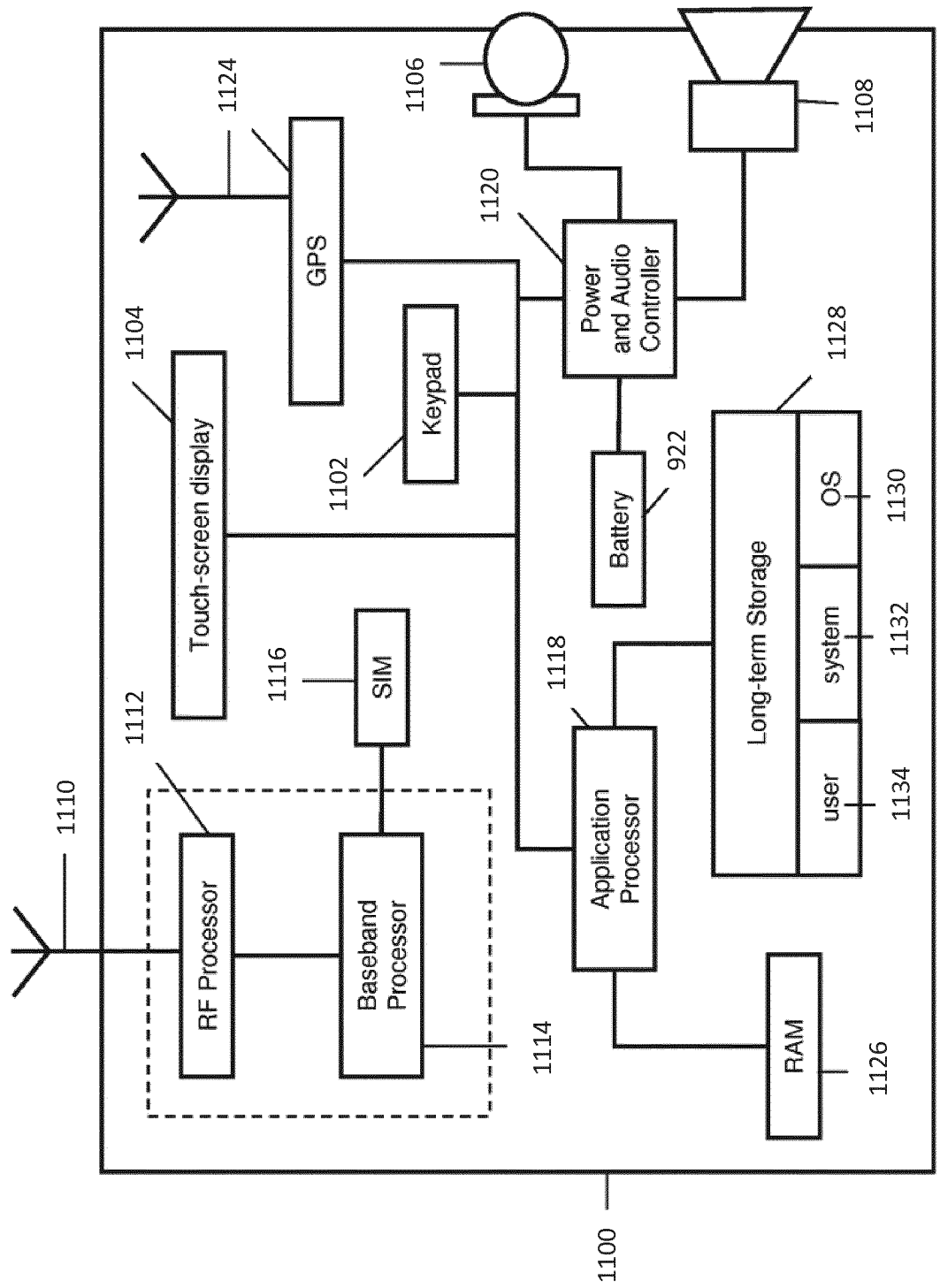

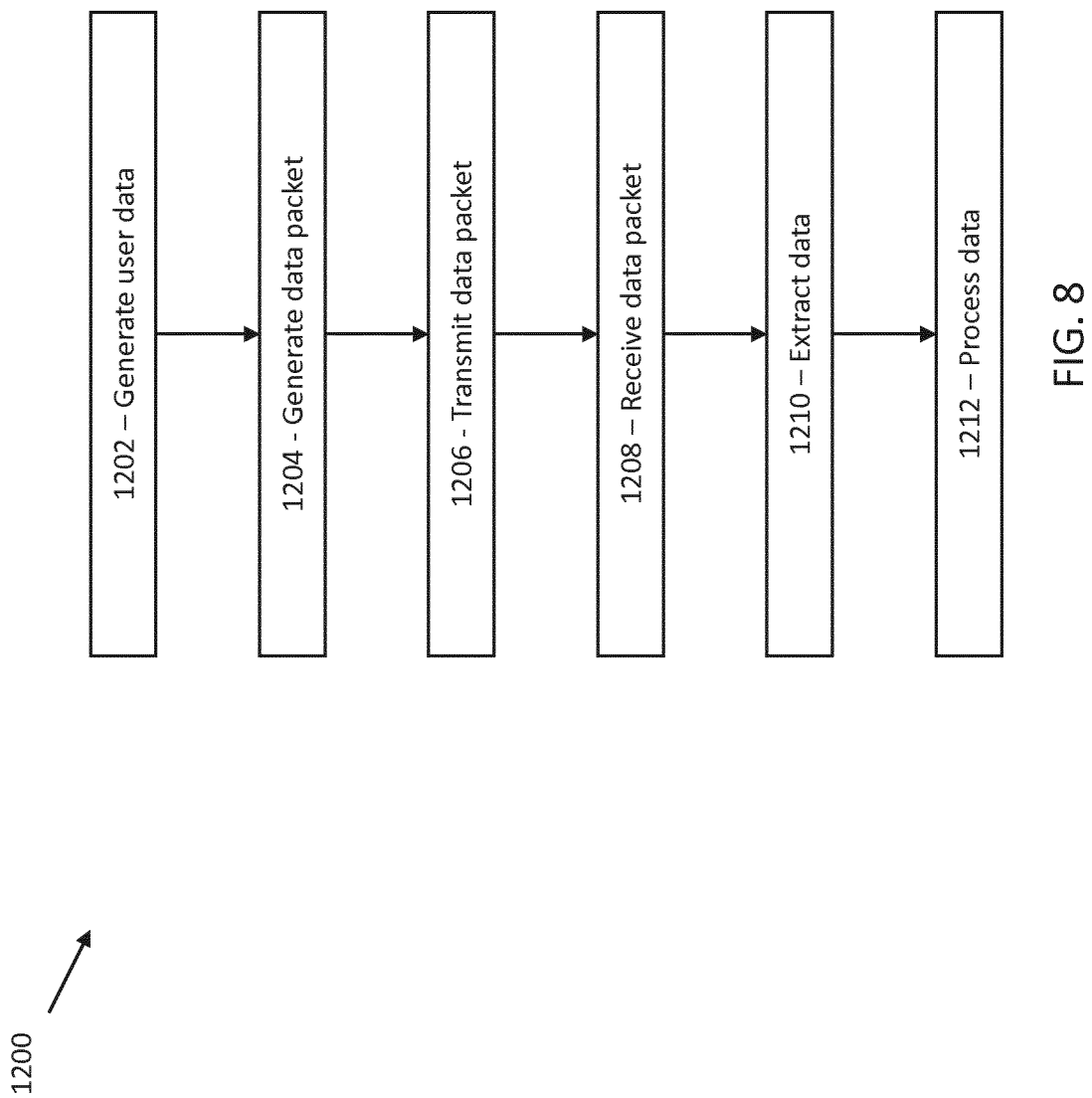

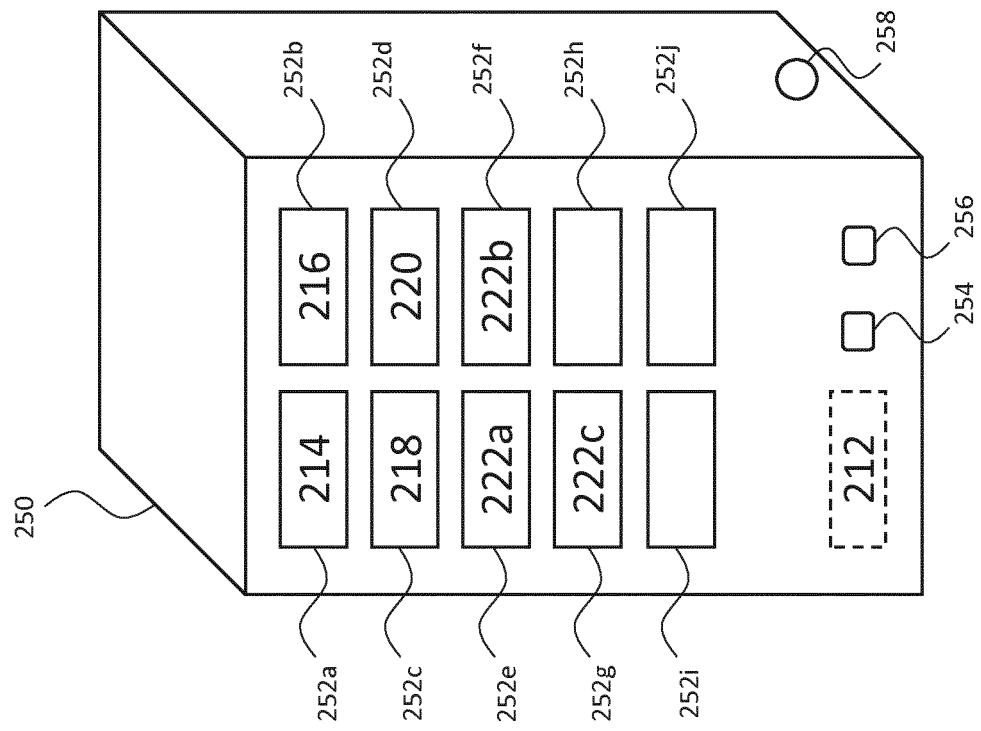

MODULAR ELECTROSURGICAL SYSTEM, AND MODULES FOR SAID SYSTEM

CROSS-REFERENCE TO RELATED APPLICATIONS

This application is a National Stage entry of International Application No. PCT/EP2019/082571, filed on Nov. 26, 2019, which claims priority to United Kingdom Patent Application No. 1820060.0, filed on Dec. 10, 2018. The disclosures of the priority applications are hereby incorporated in their entirety by reference.

TECHNICAL FIELD

The invention relates to a modular electrosurgical system for using electromagnetic (EM) radiation, such as radio frequency (RF) or microwave EM radiation, to treat biological tissue. In an embodiment, control of the modules is centralised in a remote computing device which can communicate wirelessly with the modules of the system. In an embodiment, different optional modules may be combined together with core modules to provide the system with different electrosurgical capabilities.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operators vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage is then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

FIG. 1 shows a schematic diagram of an electrosurgical apparatus 100 as set out in GB 2 486 343. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 102 followed by a power splitter 124 (e.g. a 3 dB power splitter), which divides the signal from the source 102 into two branches. One branch from the power splitter 124 forms a microwave channel, which has a power control module comprising a variable attenuator 104 controlled by controller 106 via control signal V10 and a signal modulator 108 controlled by controller 106 via control signal V11, and an amplifier module comprising drive amplifier 110 and power amplifier 112 for generating forward microwave EM radiation for delivery from a probe 120 at a power level suitable for treatment. After the amplifier module, the microwave channel continues with a microwave signal coupling module (which forms part of a microwave signal detector) comprising a circulator 116 connected to deliver microwave EM energy from the source to the probe along a path between its first and second ports, a forward coupler 114 at the first port of the circulator 116, and a reflected coupler 118 at the third port of the circulator 116. After passing through the reflected coupler, the microwave EM energy from the third port is absorbed in a power dump load 122. The microwave signal coupling module also includes a switch 115 operated by the controller 406 via control signal V12 for connecting either the forward coupled signal or the reflected coupled signal to a heterodyne receiver for detection The other branch from the power splitter 124 forms a measurement channel. The measurement channel bypasses the amplifying line-up on the microwave channel, and hence is arranged to deliver a low power signal from the probe. In this embodiment, a primary channel selection switch 126 controlled by the controller 106 via control signal V13 is operable to select a signal from either the microwave channel or the measurement channel to deliver to the probe. A high band pass filter 127 is connected between the primary channel selection switch 126 and the probe 120 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 128 connected to deliver microwave EM energy from the source 102 to the probe along a path between its first and second ports. A reflected signal returned from the probe is directed into the third port of the circulator 128. The circulator 128 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 130) back into the signal coming out of the third port (via injection coupler 132). The carrier cancellation circuit includes a phase adjustor 134 to ensure that the injected portion is 180° out of phase with any signal that breaks through into the third port from the first port in order to cancel it out. The carrier cancellation circuit also include a signal attenuator 136 to ensure that the magnitude of the injected portion is the same as any breakthrough signal.

To compensate for any drift in the forward signal, a forward coupler 138 is provided on the measurement channel. The coupled output of the forward coupler 138 and the reflected signal from the third port of the circulator 128 are connected to respective input terminal of a switch 140, which is operated by the controller 106 via control signal V14 to connect either the coupled forward signal or the reflected signal to a heterodyne receiver for detection.

The output of the switch 140 (i.e. the output from the measurement channel) and the output of the switch 115 (i.e. the output from the microwave channel) are connect to a respective input terminal of a secondary channel selection switch 142, which is operable by the controller 106 via control signal V15 in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 142. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 144 and a mixer 148 for mixing down the signal output by the secondary channel selection switch 142. The frequency of the local oscillator signal is selected so that the output from the mixer 148 is at an intermediate frequency suitable to be received in the controller 406. Band pass filters 146, 150 are provided to protect the local oscillator 144 and the controller 106 from the high frequency microwave signals.

The controller 106 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 106 via a user interface 152, as discussed above.

The RF channel shown in FIG. 1 comprises an RF frequency source 154 connected to a gate driver 156 that is controlled by the controller 106 via control signal V16. The gate driver 156 supplies an operation signal for an RF amplifier 158, which is a half-bridge arrangement. The drain voltage of the half-bridge arrangement is controllable via a variable DC supply 160. An output transformer 162 transfers the generated RF signal on to a line for delivery to the probe 120. A low pass, band pass, band stop or notch filter 164 is connected on that line to protect the RF signal generator from high frequency microwave signals.

A current transformer 166 is connected on the RF channel to measure the current delivered to the tissue load. A potential divider 168 (which may be tapped off the output transformer) is used to measure the voltage. The output signals from the potential divider 168 and current transformer 166 (i.e. voltage outputs indicative of voltage and current) are connected directly to the controller 106 after conditioning by respective buffer amplifiers 170, 172 and voltage clamping Zener diodes 174, 176, 178, 180 (shown as signals B and C in FIG. 1).

To derive phase information, the voltage and current signals (B and C) are also connected to a phase comparator 182 (e.g. an EXOR gate) whose output voltage is integrated by RC circuit 184 to produce a voltage output (shown as A in FIG. 1) that is proportional to the phase difference between the voltage and current waveforms. This voltage output (signal A) is connected directly to the controller 106.

The microwave/measurement channel and RF channel are connected to a signal combiner 184, which conveys both types of signal separately or simultaneously along cable assembly 186 to the probe 120, from which it is delivered (e.g. radiated) into the biological tissue of a patient.

SUMMARY OF THE INVENTION

At its most general, the present invention provides an electrosurgical system constructed from modules, wherein optional modules can be added and removed from core modules to change the electrosurgical capabilities of the system. Control of the modules is centralised in a remote computing device which can communicate wirelessly with the modules of the system. Each module may include a separate wireless communication interface and so be able to communicate separately with the remote computing device. Additionally or alternatively, a plurality of modules may share a single wireless communication interface. The modular electrosurgical system is operable to generate an EM signal for provision to an electrosurgical instrument for treatment of biological tissue, for example, at a treatment site near a distal assembly of the electrosurgical instrument. The remote computing device may be configured to perform real-time monitoring of the modules via feedback data received from the modules. The remote computing device may be configured to store and display (e.g. graphs and tables) data received from the modules via a user interface.

A first aspect of the invention provides a modular electrosurgical system comprising: a controller module having a wireless communication interface operable to wirelessly communicate with a remote computing device so as to receive data therefrom, the controller module being operable to provide control commands based on the received data; a signal generator module in communication with the controller module so as to receive the control commands, the signal generator module operable to generate and control electromagnetic (EM) radiation based on the control commands to form an EM signal; and a feed structure module for conveying the EM signal and having an output port for outputting the EM signal to an electrosurgical instrument, the feed structure having a signal channel for connecting the signal generator module to the output port.

The wireless communication interface enable wireless communication with the remote computing device. The wireless communication interface may be capable of communicating via one or more different protocols, such as, 3G, 4G, 5G, GSM, WiFi, Bluetooth™ and/or CDMA. The wireless communication interface may include communication hardware for the transmission and reception of data signals, such as, a transmitter and a receiver (or a transceiver). Also, the communication hardware may include an antenna and an RF processor which provides an RF signal to the antenna for the transmission of data signals, and the receipt therefrom. The wireless communication interface may also include a baseband processor, which provides data signals to and receives data signals from the RF Processor. The precise construction of the wireless communication interface may vary between embodiments, as would be understood by the skilled person.

The electromagnetic radiation (or energy) may comprise radiofrequency (RF) energy and/or microwave frequency energy. The signal generator module may include any device capable of delivery RF EM energy or microwave frequency EM energy for treatment of biological tissue. For example, the generator described in WO 2012/076844 (incorporated herein by reference) may be used.

The feed structure may be a coaxial feed cable comprising an inner conductor, an outer conductor coaxial with the inner conductor and a second dielectric material separating the inner and outer conductors, the coaxial feed cable being for conveying an RF signal and/or a microwave signal. In an embodiment, the feed structure module may include the feed structure described in WO 2012/076844.

In an embodiment, the controller module further comprises a processor in communication with the wireless communication interface so as to receive the received data, the processor being operable to generate the control commands based on the received data. The processor may be a microprocessor.

In an embodiment, the controller module is operable to transmit the control commands via the wireless communication interface to the remote computing device.

In an embodiment, the controller module is operable to decrypt data received at the wireless communication interface, and to encrypt data transmitted from the wireless communication interface.

In an embodiment, the controller module comprises a watchdog for monitoring a potential error condition of the system, the watchdog being operable to generate an alarm signal when the error condition occurs. The watchdog may be a fault detection device which is independent of a processor of the controller module.

In an embodiment, the system further comprises a sensor operable to monitor operation of part of the system and to generate corresponding sensor data, and wherein the watchdog is operable to generate the alarm signal based on a comparison between the sensor data and one or more sensor thresholds. For example, the sensor may be a temperature sensor coupled to part of the system (e.g. a processor of the controller module) so as to generate temperature measurements based on a temperature of the part. The watchdog can then compare the temperature measurements from the sensor with temperature limits and shut down the system if the temperature measurements move outside the limits. Alternatively, the sensor may be a voltage sensor which generates voltage measurements based on a voltage across a part of the system (e.g. a cooling fan which provides active cooling to the processor). The watchdog can then compare the voltage measurements from the sensor with voltage limits and shut down the system if the voltage moves outside the limits.

In an embodiment, the controller module is operable to transmit the alarm signal via the wireless communication interface to the remote computing device. In this way, the remote computing device can handle the system's response to the fault.

In an embodiment, the watchdog is operable to generate the alarm signal when the wireless communication interface losses communication with the remote computing device for at least a preset time period. In an embodiment, the preset limit may be at least ten seconds.

In an embodiment, the controller module is operable to generate the control commands based on the alarm signal. In this way, the controller module can handle the system's response to the fault.

In an embodiment, the system further comprises a signal detector module coupled to the signal channel so as to sample a signal characteristic on the signal channel and to generate therefrom a detection signal indicative of the signal characteristic.

In an embodiment, the controller module is operable to generate the control commands based on the detection signal. As such, the EM signal can be adapted based on tissue characteristics to promote efficient transfer of EM radiation into tissue.

In an embodiment, the controller module is operable to transmit the detection signal via the wireless communication interface to the remote computing device. As such, the remote computing device can control adaption of the EM signal based on tissue characteristics to promote efficient transfer of EM radiation into tissue. Also, tissue characteristics (e.g. tissue type) can be presented to a user via a user interface of the remote computing device.

In an embodiment, the feed structure module further comprises a tuner connected to the signal channel for controlling the energy delivered by the EM signal, the tuner comprising an adjustable impedance element that is controllable by the controller module based on the detection signal. In an embodiment, the tuner may include the RF tuner described in WO 2012/076844. In an embodiment, the tuner may include the impedance adjuster described in WO 2012/076844.

In an embodiment, the signal generator module further comprises a pulse generator that is controllable by the controller module based on the control commands to generate pulsed EM radiation from the EM radiation, wherein the EM signal includes the pulsed EM radiation. In this way, the signal generator module may suitable for electroporation. In an embodiment, the signal generator module includes the signal generator described in GB 2 563 386, which is incorporated by reference.

In an embodiment, the system further comprises a fluid feed module having a fluid feed structure in fluid communication with a fluid port for outputting fluid to the electrosurgical instrument, the fluid feed module being controllable by the controller module based on the control commands to supply and control a fluid flow via the fluid feed structure to the fluid port. As such, the system can be used to provide fluid (e.g. gas or liquid) to a treatment site near a distal end (or distal assembly) of the electrosurgical instrument. The fluid may be used with the EM signal to generate plasma, for example, thermal or non-thermal plasma. In an embodiment, the fluid feed module includes the gas feed apparatus described in WO 2012/076844. Additionally, the fluid feed module may include a pump or suction device such that fluid can be extracted from the treatment site.

In an embodiment, the fluid feed module further comprises a temperature control element coupled to the fluid feed structure and controllable by the controller module based on the control commands to adjust a temperature of the fluid flow in the fluid feed structure. In this way, the fluid can be heated up or cooled prior to being delivered to a distal end (or distal assembly) of the instrument. This may be useful in the generation of plasma. Also, the fluid (e.g. liquid) may be cooled so as to form a tissue-freezing fluid in order to perform a cryoablation function.

In an embodiment, the system further comprises one or more additional signal generator modules operable to generate and control additional EM radiation based on the control commands to form one or more additional EM signals, the or each additional signal generator module generating EM radiation at a different frequency to the signal generator module and to each other additional signal generator module, and wherein the feed structure module has one or more additional signal channels for coupling the or each additional signal generator module to the output port. As such, both RF and microwave energy may be delivered, simultaneously or separately, to a treatment site near the distal assembly of the instrument. Also, different frequencies of microwave and RF can also be provided in order to treat different conditions.

In an embodiment, the signal channel and the or each additional signal channel comprise physically separate signal pathways, and wherein the feed structure module comprises a signal combining circuit having one or more inputs, each input connected to a different one of the physically separate signal pathways, the signal combining circuit having an output connected to a common signal pathway for conveying the EM signal and the or each additional EM signal, separately or simultaneously, along a single channel to the output port.

In an embodiment, the signal combining circuit includes a switching device for connecting one or more of the signal channel and the or each additional signal channel to the common signal pathway, wherein the switching device is controllable by the controller module based on the control commands.

In an embodiment, the system further comprises a case for containing multiple modules of the system, the case comprising multiple sockets for receiving the multiple modules. A socket may provide various connections for a module inserted into the socket. For example, the socket may include a power connector which is located so as to engage with a cooperating power connector on the module when the module is inserted into the socket. In this way power may be provided to the module for operation. Additionally or alternatively, similar connectors may be provided for supplying/extracting various signals to/from the module, such as, EM signals, fluid signals, and detection signals. The case may also include a connector for connecting an EM signal to the instrument, and a connector for connecting a fluid flow to the instrument. The case may also include a power connector for providing power (e.g. from a mains supply) to the case and to modules received into sockets of the case.

In an embodiment, the system further comprises an electrosurgical instrument arranged to deliver EM radiation from a distal end (or distal assembly) thereof, the electrosurgical instrument having an instrument feed structure for conveying the EM signal to the distal end, the instrument feed structure having an instrument signal channel for connecting the distal end to the output port. In an embodiment, the instrument feed structure module includes the feed structure described in WO 2012/076844.

The electrosurgical instrument may be any device which in use is arranged to use RF EM energy or microwave frequency EM energy for the treatment of biological tissue. The electrosurgical instrument may use the RF EM energy and/or microwave frequency EM energy for any or all of resection, coagulation and ablation. For example, the instrument may be a resection device, but alternatively may be any of a pair of microwave forceps, a snare that radiates microwave energy and/or couples RF energy, and an argon beam coagulator.

The instrument may include an instrument fluid feed structure or conduit for delivering fluid (e.g. saline) to the instrument tip. The instrument fluid feed structure may comprise a passageway through the instrument for delivering fluid to the treatment site.

The instrument feed structure and the instrument fluid feed structure may form part of a multi-lumen conduit assembly for delivering RF and/or microwave frequency energy and fluid (liquid or gas) to the instrument. In an embodiment, the instrument fluid feed structure may include the gas supply tube described in WO 2012/076844.

In an embodiment, the system further comprises a remote computing device having: at least one processor; and at least one memory including computer program code; the at least one memory and the computer program code configured to, with the at least one processor, cause the remote computing device at least to: generate input data based on user input, the input data specifying at least one operating parameter of the signal generator module; generate a data packet for wireless transmission to the controller module, the data packet including the at least one operating parameter; and transmit the data packet to the controller module via a wireless communication channel. The remote computing device may be a laptop computer, tablet computer or smartphone.

A second aspect of the invention provides a signal generator module for a modular electrosurgical system, the signal generator module comprising: a controller having a wireless communication interface operable to wirelessly communicate with a remote computing device so as to receive data therefrom, the controller being operable to provide control commands based on the received data; a signal generator in communication with the controller so as to receive the control commands, the signal generator operable to generate and control electromagnetic (EM) radiation based on the control commands to form an EM signal; and a feed structure for conveying the EM signal and having an output port for outputting the EM signal to an electrosurgical instrument, the feed structure having a signal channel for connecting the signal generator to the output port.

A third aspect of the invention provides fluid feed module for a modular electrosurgical system, the fluid feed module comprising: a controller having a wireless communication interface operable to wirelessly communicate with a remote computing device so as to receive data therefrom, the controller being operable to provide control commands based on the received data; a fluid feed structure in fluid communication with a fluid port for outputting fluid to an electrosurgical instrument, the fluid feed structure being controllable by the controller based on the control commands to supply and control a fluid flow to the fluid port.

A fourth aspect of the invention provides a signal combining module for a modular electrosurgical system, the signal combining module comprising: a controller having a wireless communication interface operable to wirelessly communicate with a remote computing device so as to receive data therefrom, the controller being operable to provide control commands based on the received data; a plurality of input ports for receiving a plurality of input electromagnetic (EM) signals; an output port for transmitting an output EM signal to an electrosurgical instrument; and a feed structure comprising a plurality of separate signal pathways coupled to the plurality of input ports for conveying the plurality of input EM signals to a switching device, the feed structure having a common signal pathway connected to the output port, wherein the switching device is configured to selectively connect one or more of the plurality of separate signal pathways to the common signal pathway based on the control commands.

A fifth aspect of the invention provides a modular electrosurgical system comprising: a signal generator module according to the second aspect; an electrosurgical instrument arranged to deliver EM radiation from a distal end (or distal assembly) thereof, the electrosurgical instrument having an instrument feed structure for conveying the EM signal to the distal end, the instrument feed structure having an instrument signal channel for coupling the distal end to the output port of the signal generator module; and a remote computing device for wirelessly sending data to the wireless communication interface of the signal generator module based on user input data received by the remote computing device.

In an embodiment, the system further comprises: an additional signal generator module according to the second aspect; and a signal combining module according to the fourth aspect; wherein the output port of the signal generator module is connected to a first one of the plurality of input ports of the signal combining module, and the output port of the additional signal generator module is connected to a second one of the plurality of input ports of the signal combining module, and wherein the output port of the signal combining module is connected to the instrument feed structure.

In an embodiment, the system further comprises: a fluid feed module according to the third aspect; a fluid feed structure connected to supply the fluid flow from the fluid port of the fluid feed module to the distal end of the electrosurgical instrument.

It is noted that the further features and advantages mentioned above with reference to the first aspect are equally applicable and are restated in respect of the second to fifth aspects.

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

Herein, the terms "proximal" and "distal" refer to the ends of the energy conveying structure further from and closer to the treatment site respectively. Thus, in use the proximal end is closer to a generator for providing the EM energy, whereas the distal end is closer to the treatment site, i.e. the patient.

BRIEF DESCRIPTION OF THE DRAWINGS

Examples embodying the invention as discussed in detail below with reference to the accompanying drawings, in which:

FIG. 7 is a schematic diagram of a remote computing device, in accordance with an embodiment;

FIG. 8 is a flow diagram of a method of operation of a remote computing device in accordance with another embodiment; and FIG. 9 is a schematic diagram of a case containing modules of the modular electrosurgical system of FIG. 2.

DETAILED DESCRIPTION; FURTHER OPTIONS AND PREFERENCES

Various embodiments relate to a modular electrosurgical system for using electromagnetic (EM) radiation, such as radio frequency (RF) or microwave EM radiation, to treat biological tissue. In an embodiment, control of the modules is centralised in a remote computing device which can communicate wirelessly with the modules of the system. In an embodiment, different optional modules may be combined together with core modules to provide the system with different electrosurgical capabilities.

Various aspects of the present invention are presented below in the context of an electro-surgery environment that provides a modular electrosurgical system for use in endoscopic procedures involving the controlled delivery of EM energy, for example, RF and microwave energy. Such EM energy may be useful in the removal of polyps and malignant growths. However, it is to be understood that the aspects of the invention presented herein need not be limited to this particular application. Also, they may be equally applicable in embodiments where only RF energy is required, or where only RF energy and fluid delivery is required.

Figure 2:
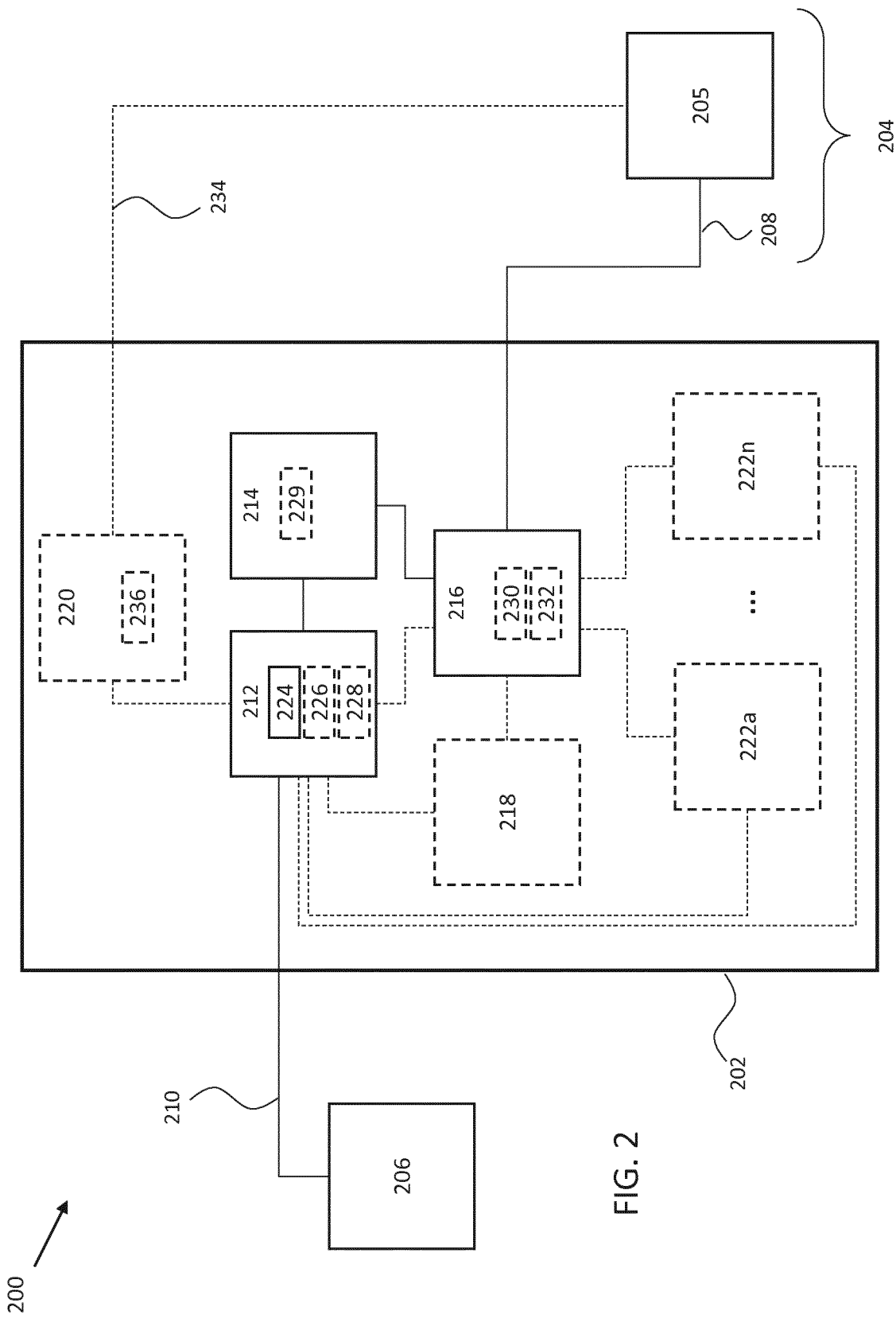
FIG. 2 is a schematic diagram of a modular electrosurgical system, in accordance with an embodiment.

FIG. 2 is a schematic diagram of a modular electrosurgical system 200, in accordance with an embodiment. The modular system 200 includes a plurality of modules 202, an electrosurgical instrument 204, and a remote computing device 206.

In an embodiment, the plurality of modules 202 are housed within a single physical structure, housing or case. In example case is described below with reference to FIG. 9. However, it is to be understood that in at least some other embodiments, the plurality of modules 202 may be included in multiple cases, or without a case(s).

The electrosurgical instrument 204 is connected to the plurality of modules 202. The electrosurgical instrument 204 is arranged or configured to deliver EM radiation from a distal end (or distal assembly) 205 in order to treat biological tissue located at a treatment site at or near to the distal end 205. The electrosurgical instrument 204 may be any device which in use is arranged to use EM energy (e.g. RF energy, microwave energy) for the treatment of biological tissue. The electrosurgical instrument 204 may use the EM energy for any or all of resection, coagulation and ablation. For example, the instrument 204 may be a resection device, a pair of microwave forceps, or a snare that radiates microwave energy and/or couples RF energy, and an argon beam coagulator.

The electrosurgical instrument 204 includes an instrument feed structure 208 for conveying EM radiation (e.g. an EM signal) to the distal end 205. The instrument feed structure 208 has an instrument signal channel for connecting the distal end 205 to one or more modules within the plurality of modules 202, as described in more detail below. The instrument feed structure 208 may be provided within a cable assembly for insertion through an instrument channel of an endoscope. To achieve this, the cable assembly may have an outer diameter of 9 mm or less, e.g. 2.8 mm or less for a flexible video colonoscope. The cable assembly may include an outer flexible sleeve which provides a protective structure around the instrument feed structure and provides a means by which torque can be transferred from proximal end of the cable assembly to a distal end of the cable assembly.

The remote computing device 206 is a wireless computing device such as a laptop, a smartphone, a tablet computer, and the like. The remote computing device 206 is capable of wirelessly communicating with the plurality of modules 202 via a wireless communication channel 210 so as to control the operation of the plurality of modules 202. As such, control of the system 200 may be centralised in the remote computing device 206. To this end, the remote computing device 206 includes a wireless communication interface operable to wirelessly communicate with a module of the plurality of modules 202 so as to send instructions thereto. A specific embodiment of the remote computing device 206 is described below with reference to FIG. 7. Also, an example method of operation of the remote computing device 206 is described in more detail below with reference to FIG. 8.

The modules of the plurality of modules 202 will now be described in detail.

The plurality of modules 202 includes a controller module 212, a signal generator module 214, and a feed structure module 216. These may be the core modules of the system 200. Additionally, the plurality of modules 202 may include further optional modules: a signal detector module 218, a fluid feed module 220, and one or more additional signal generator modules 222a-222n. The optional nature of these modules is indicated in FIG. 2 by dashed lines. Also, the various connections between the different modules is shown in FIG. 2.

The core modules of the plurality of modules 202 will now be described in detail.

The controller module 212 has a wireless communication interface 224 operable to wirelessly communicate with the remote computing device 206, so as to receive instructions or data therefrom. The controller module 212 is operable to provide control commands based on the received data. For example, in one embodiment, the control commands may be all or part of the received data and, as such, the controller module 212 may forward the received data as the control commands. Also, the forwarding may involve removing part of the received data before forwarding. For instance, the received data may comprise a data packet which includes both the control commands and communication information, wherein the communication information is used to direct the data packet from its source (e.g. the remote computing device 206) to its destination (e.g. the controller module 212). The wireless communication channel 210 may be a direct channel between the remote computing device 206 and the controller module 212, but it may also be an indirect channel that includes, for example, one or more wired or wireless networks, such as, the Internet, a local area network, and/or a wide area network. In any case, the controller module 212 may remove or strip out this communication information (and, for example, any other information) such that only the control commands remain. Additionally or alternatively, however, the controller module 212 may include a processor 226 (e.g. a microprocessor) which is coupled to the wireless communication interface 224 so as to receive the received data. In use, the processor 226 may generate the control commands based on the received data. That is, the received data may include none of the control commands, or only part of the control commands, such that the processor 226 generates at least some of the control commands itself. It is to be understood the control commands are in a format that the module can understand and execute so as to perform one or more module functions.

The wireless communication interface of the controller module 212 and the remote computing device 206 enable the controller module 212 to wirelessly communicate with the remote computing device 206. Each wireless communication interface may be capable of communicating via one or more different protocols, such as, 3G, 4G, 5G, GSM, WiFi, Bluetooth™ and/or CDMA. In any case, the controller module 212 and the remote computing device 206 may communicate with each other via the same protocol, such as, WiFi. Each wireless communication interface may include communication hardware for the transmission and reception of data signals, such as, a transmitter and a receiver (or a transceiver). Also, the communication hardware may include an antenna and an RF processor which provides an RF signal to the antenna for the transmission of data signals, and the receipt therefrom. Each wireless communication interface may also include a baseband processor, which provides data signals to and receives data signals from the RF Processor. The precise construction of the wireless communication interface may vary between embodiments, as would be understood by the skilled person.

In an embodiment, the controller module 212 is operable to decrypt the data which is received at the wireless communication interface 224, for example, from the remote computing device 206. Also, the controller module 212 is operable to encrypt data which is transmitted by the wireless communication interface 224, for example, to the remote computing device 206. For instance, where the controller module 212 generates the control commands, the controller module 212 may transmit those generated control commands via the wireless communication interface 224 to the remote computing device 206, as will be described in more detail later. Where the controller module 212 includes the processor 226, the encryption and decryption processes may be performed by the processor 226. Alternatively, the controller module 212 may include a separate encryption device for performing encryption and decryption. It is to be understood that any encryption protocol could be used, as would be known to the skilled person. However, given the electrosurgical nature of the invention, a medical encryption protocol may be preferable. An advantage of requiring that data be transmitted to/from the controller module 212 in encrypted form, is that a malicious party would find it more difficult or impossible to hack the electrosurgical system 200 so as to take control of the electrosurgical instrument 204. As such, system security and patient safety is improved.

In an embodiment, the controller module 212 includes a watchdog (or fault detection unit) 228 for monitoring a range of potential error conditions which could result in the system 200 not performing to its intended specification. The watchdog 228 is operable to generate an alarm signal when one of the potential error conditions occurs. For example, the watchdog 228 may monitor a status of communication between the wireless communication module 224 and the remote computing device 206, and a potential error condition may be a breakdown in communication between the controller module 212 and the remote computing device 206 for a duration above a preset threshold or time-period. For example, the watchdog 228 may generate an alarm signal when the wireless communication module 224 has been unable to communicate with the remote computing device 206 for more than ten seconds. It is to be understood that different time-periods could be used in different embodiments.

In an embodiment, the controller module 212 includes one or more sensors which monitor the operation of various parts of the system 200, and the watchdog 228 may generate alarm signals when the outputs of these sensors moves outside of preset limits. For example, the controller module 212 may include one or more temperature sensors operable to generate temperature measurements based on a temperature of part of the controller module 212, such as, the processor 226 or a memory of the controller module 212. The watchdog 228 may then be operable to generate an alarm signal based on a comparison between the temperature measurements and one or more preset temperature limits, to indicate that the part is overheating. Additionally or alternatively, a different type of sensor (e.g. a voltage or current sensor) may be provided to monitor the operation of a fan which provides active cooling to the processor or memory, such that the watchdog 228 generates an alarm signal if the sensor indicates that the fan has malfunctioned (e.g. it is using no voltage or current). Additionally or alternatively, a sensor may monitor a voltage level of a DC power supply of the controller module 212, and the watchdog 228 may generate an alarm signal if the voltage level drifts out of a predetermined accepted range of operation. It is to be understood that the controller module 212 can contain different types of sensor which monitor the operation of different elements of the controller module, and the watchdog may monitor the outputs of these sensors and generate an alarm signal if any one of these outputs moves outside of preset limits. Additionally, the controller module 212 may contain sensors which monitor the operation of other modules, and the watchdog may monitor the outputs of these sensors and generate an alarm signal if any one of these outputs moves outside of preset limits.

The controller module 212 may handle an alarm signal in a number of different ways. For example, the controller module 212 may cause the watchdog 228 to transmit the alarm signal via the wireless communication interface 224 to the remote computing device 206. In this way, the remote computing device 206 can keep a record or log of when faults occur. Also, the watchdog 228 may include in the alarm signal a reference to a type of fault to which the alarm signal relates such that the remote computing device 206 can include this information in the log. Also, the remote computing device 206 may externally control the response of the system 200 based on the alarm signal. For example, the remote computing device 206 may send particular control commands to the controller module 212 based on the alarm signal, for example, so as to shut down the electrosurgical system 200 in a safe manner. In this way, the remoted computing device 206 may externally control the response of the system 200 based on the alarm signal. Additionally or alternatively, the controller module 212 (e.g. processor 226) may itself generate control commands based on the alarm signal. In this way, the controller module 212 may internally control the response of the system 200 based on the alarm signal. This internal control mechanism maybe particularly suitable for the loss of communication fault described earlier. On the other hand, the external control mechanism maybe particularly suitable for overheating faults described earlier. Therefore, a hybrid model may be adopted in which some faults are handled internally whereas some other faults are handled externally.

In an embodiment, where the controller module 212 includes the processor 226, the watchdog 228 includes an independent processor (e.g. a microprocessor) so that the watchdog 228 can confirm that the processor 226 is functioning correctly, i.e. raise an alarm signal if the processor 226 malfunctions (e.g. uses no voltage or current). Alternatively, the watchdog 228 may be implemented in software which is executed by the processor 226 of the controller module 212, i.e. no separate hardware processor may be included.

In summary, therefore, the controller module 212 receives data from the remote computing device 206 and, based on this received data, provides control commands to the signal generator module 214.

Figure 1:
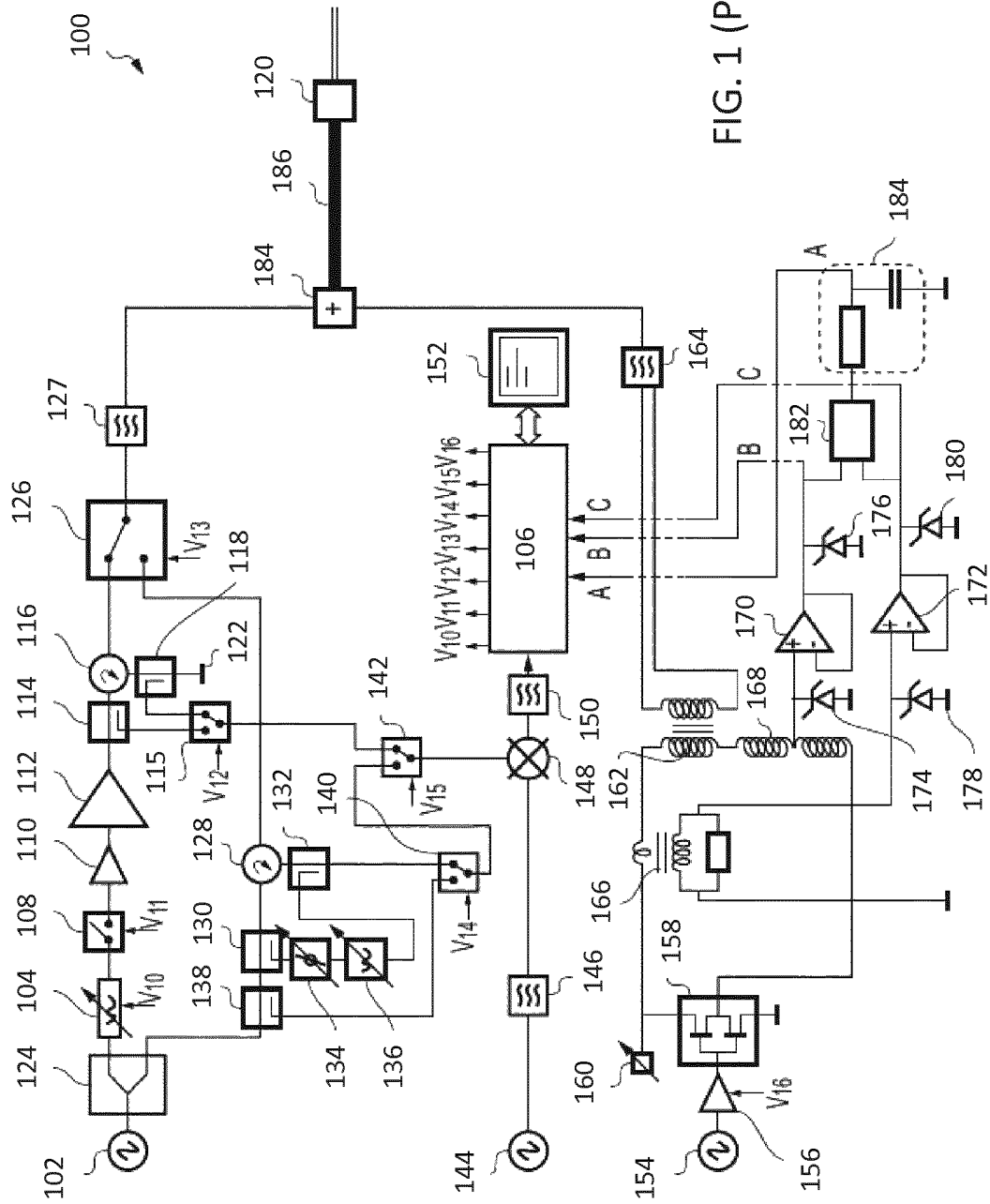
FIG. 1 is a schematic diagram of a prior art electrosurgical apparatus.

The signal generator module 214 is in communication with the controller module 212 so as to receive the control commands. For example, the signal generator module 214 may be coupled to the controller module 212 via a wired connection or cable. In use, the signal generator module 214 is operable to generate and control EM radiation based on the control commands to form an EM signal. The signal generator module may be any device capable of delivery EM energy for treatment of biological tissue. For example, the signal generator module 214 may be an RF signal generator module capable of generating and controlling RF EM radiation, for example, having a frequency of 100-500 KHz, or 300-400 MHz. Additionally, the RF signal generator module may include a bipolar or monopolar RF signal generator. In an embodiment, the signal generator module may include the RF EM signal generator portion of FIG. 1 (e.g. 154, 156, 158, 160 and 162). Alternatively, the signal generator module 214 may be a microwave signal generator module capable of generating and controlling microwave EM radiation, for example, having a frequency of 433 MHz, 915 MHz, 2.45 GHz, 5.8 GHz, 14.5 GHz, 24 GHz, or 30 to 31 GHz. In an embodiment, the signal generator module may include the microwave signal generator portion of FIG. 1 (e.g. 102, 104, 108, 110, and 112). Alternatively, the signal generator module 214 may be an electroporation signal generator module capable of generating and controlling EM radiation having a low frequency, for example, 30 to 300 kHz.

The signal generator module 214 generates EM radiation based on the control commands. As such, example control commands may include an instruction for the signal generator module 214 to turn ON so as to generate EM radiation at its operational frequency, i.e. 433 MHz in the case of a 433 MHz microwave signal generator module. Also, the control commands may include an instruction for the signal generator module 214 to turn OFF so as to stop generating the EM radiation. Additionally or alternatively, the control commands could include other commands which specify other parameters of the EM radiation, for example, a duration that the signal generator module should generate EM energy, or a power (or amplitude) of the generated EM energy.

In an embodiment, the signal generator module 214 includes a pulse generator 229 that is controllable by the controller module 212 based on the control commands to generate pulsed EM radiation from the EM radiation. Accordingly, the signal generator module 214 may be an electroporation signal generator module. For example, the EM radiation which is generated and controlled by the signal generator module 214 is operated on by the pulse generator 229 so as to generate pulsed EM radiation which forms the EM signal that is received by the feed structure module 216. In this way, the signal generator module 214 is modified so as to provide a pulsed EM signal. The controller module 212 may control the pulse generator 229, via the control commands, to simply turn "ON" or "OFF" so that the signal generator module 214 generates an EM signal which is pulsed or continuous, respectively. Alternatively, the control commands may specify one or more pulse parameters, such as, a duty cycle, a pulse width (e.g. 0.5 ns to 300 ns), a rise time (e.g. Pico second or Nano second), or an amplitude (e.g. up to 10 kV). Additionally, the control commands may instruct the pulse generator to deliver a single pulse, a pulse train (e.g. number of pulses, or duration), or a burst of pulses (e.g. burst duration, number of pulses in burst, period between bursts).

In an embodiment, the signal generator module 214 includes one or more sensors which monitor the operation of different elements of the signal generator module 214 and send measurements to the controller module 212. As mentioned above, the controller module 212 (via the watchdog 228) can then compare these measurements to acceptable limits and generate an alarm signal if any one of these different elements develops a fault. For example, the signal generator module 214 may include a temperature sensor operable to generate temperature measurements based on a temperature of part of the signal generator module (e.g. an oscillator or an amplifier). The watchdog 228 then generates the alarm signal based on a comparison between the temperature measurements and one or more preset temperature limits.

In summary, the signal generator module 214 generates and controls EM radiation based on the control commands to form the EM signal. The frequency of the EM radiation is dependent on signal generator's type. The feed structure module 216 receives the EM signal from the signal generator module 214.

The feed structure module 216 is in communication with the signal generator module 214 so as to receive the EM signal. The feed structure module 216 includes a signal channel which conveys the EM signal from the signal generator module 214 to an output port of the feed structure module 216. The output port is for outputting the EM signal to the electrosurgical instrument 204 and, as such, the output port may connect to the instrument feed structure 208 via cooperating connectors on the output port and a proximal end of the instrument feed structure 208. The feed structure module 216 may be coupled to the signal generator module 214 via a cable assembly which includes the signal channel. Also, the cable assembly may terminate in the output port. As such, in an embodiment, the feed structure module 216 may be a cable assembly connecting the signal generator module 214 to the instrument feed structure 208 and including a signal channel for conveying the EM signal.

In view of the above, the remote computing device 206, the controller module 212, the signal generator module 214, the feed structure module 216 and the electrosurgical instrument 204 cooperate to provide a modular electrosurgical system which generates an EM signal to treat biological tissue. In an embodiment, the controller module 212, the signal generator module 214 and the feed structure module 216 maybe referred to as core modules of the plurality of modules 202.

The optional modules 218, 220 and 222 of the plurality of modules 202 will now be described in detail.

The signal detector module 218 is configured to sample a signal characteristic on the signal channel of the feed structure module 216, and to generate a detection signal which is indicative of the signal characteristic. For example, the signal generator module 214 may be an RF signal generator module, and the signal characteristic may be a voltage or a current present on the signal channel. Alternatively, the signal generator 214 may be a microwave signal generator module, and the signal characteristic may be a forward power or a reflected power present on the signal channel. In an embodiment, the signal generator module 214 may be configured to deliver a low power EM signal for the purposes of signal detection, and this low power signal may be referred to as a measurement signal, since it is generated for the purposes of measuring biological tissue at the distal end 205 of the electrosurgical instrument 204. Alternatively, an additional signal generator module 222, which will be described later, may be configured to provide the measurement signal. It is to be understood that the signal detector module 218 measures the signal channel and, as such, measures both signals emitted by the signal generator module 214, and signals which are reflected back to the feed structure module 216, for example, by biological tissue at a treatment site near to the distal end 205. Therefore, the measured signal characteristics are indicative of the biological tissue and, as such, the detection signal varies with tissue characteristics. In this way, the detection signal can be used to determine tissue characteristics (e.g. a tissue type).

In an embodiment, the controller module 212 is in communication with the signal detector module 218 so as to receive the detection signal. For example, the controller module 218 may be connected to the signal detection module 218 via a wired connection or cable. Also, the controller module 212 is operable to generate the control commands for the signal generator module 212 based on the detection signal. It is to be understood that the detection signal may be used (e.g. by the controller module 212 or remote computing device 206) to determine a characteristic of tissue at the treatment site, for example, it may indicate that the tissue is healthy or cancerous.

In use, the signal detector module 218 may provide a mechanism for the electrosurgical system 200 to dynamically respond to biological tissue being treated by the electrosurgical instrument 204. For example, the signal generator module 214 may be a microwave signal generator module, and the measured signal characteristic may include forward and reflected power sampled on the microwave signal channel of the feed structure module 216. Based on the forward and reflected power, a return loss measured on the signal channel may be between −6 dB and −10 dB. This return loss may be indicative of a bleed. The controller module 212 (or the remote computing device 206), may determine this return loss, and further determine that it indicates a bleed, and then generate control commands for the microwave signal generator module to deliver a microwave EM signal with an appropriate (e.g. increased) power level and/or duty cycle until the bleed has been stemmed. Stemming of the bleed may be indicated by a change in the return loss measured from the reflected power. In an alternative embodiment, the signal generator module 214 may be an RF signal generator module, and the measured signal characteristic may include voltage (or current) sampled on the RF signal channel of the feed structure module 216. The indication of the onset of a bleed may also be provided by a change in measured voltage/current. As such, any cutting action of the RF signal generator module may be stopped so that the bleed can be addressed, for example, by a microwave signal generator module.

Additionally or alternatively, the controller module 212 is operable to transmit the detection signal from the wireless communication interface, for example, to the remote computing device 206. Accordingly, the remote computing device 206 is operable to generate control commands based on the detection signal, and then send those control commands to the controller module 212 for execution. It may be advantageous to have the remote computing device 206 generate the control commands because the remote computing device 206 may have more processing power than the controller module 212. Alternatively, it may be advantageous to have the controller module 212 generate the control commands because it may be significantly faster to transfer data from the controller module 212 directly to the signal generator module 214, rather than via the remote computing device 206. In an embodiment, both options may be available and the choice of whether to generate the control commands at the signal generator module 214 or at the controller module 212 is situation dependent. In any case, the detection signal may be used by the remote computing device 206 and/or controller module 212 to dynamically adjust system performance based on biological tissue being treated. These adjustments may improve treatment and patient safety.

In an embodiment, the feed structure module 216 further comprises a tuner 230 connected to the signal channel for controlling the energy delivered by the EM signal. The tuner 230 includes an adjustable impedance element that is controllable by the controller module 212 based on the detection signal. In an embodiment, the controller module 212 is connected to the feed structure module 216 (and tuner 230) via a wired connection or cable.

The tuner 230 may function to promote efficient transfer of EM radiation into tissue. For example, information from the signal channel may be used to determine the adjustment of the adjustable impedance on the signal channel to provide dynamic power matching between the electrosurgical instrument 204 and the tissue. This ensures efficient and controllable energy transfer between the electrosurgical system 200 and the biological tissue.

In an embodiment, the adjustable impedance element may be an adjustable reactance (e.g. capacitance or inductance). For example, the adjustable reactance may include a plurality of reactive elements, wherein each reactive element has a fixed reactance and is independently switchable into or out of connection with the signal channel according to a respective control command from the controller module 212. Alternatively, each reactive element may have a variable reactance that is independently controllable according to a respective control command from the controller module 212. Alternatively, the adjustable reactance may be provided by a variable capacitor and/or a variable inductor, and the controller module 212 includes a self-adjusting feedback loop arranged to generate a control command for setting the reactance of the variable capacitor or the variable inductor. Such embodiments may be particularly suitable where the signal generator module 214 is an RF signal generator module and the signal channel is an RF signal channel.

In another embodiment, the adjustable impedance element may be an impedance adjuster having an adjustable complex impedance that is controllable by the controller module 212. Such an embodiment may be particularly suitable where the signal generator module 214 is a microwave signal generator module and the signal channel is a microwave signal channel.

In an embodiment, the signal detector module 218 or the feed structure module 216 includes one or more sensors which monitor the operation of different elements of the respective module and send measurements to the controller module 212. As mentioned above, the controller module 212 (via the watchdog 228) can then compare these measurements to acceptable preset limits and generate an alarm signal if any one of these different elements develops a fault.

Each additional signal generator module 222 is analogous to the signal generator module 214 in the sense that each additional signal generator module 222 is operable to generate and control EM radiation based on control commands from the controller module 212 to form an EM signal. Further, in order to function with additional signal generator modules 222, the feed structure module 216 has one or more additional signal channels for coupling each additional signal generator module 222 to the output port of the feed structure module 216. These additional signal channels may be included in the same physical structure (e.g. cable) as the previously described signal channel. In an embodiment, the feed structure 216 functions to combine together the EM signal from the signal generator module 214 with the EM signal from each additional signal generator module 222 such that they are all output from the output port, via the instrument feed structure 208, to the distal end 205 of the electrosurgical instrument 204.

It is to be understood that the signal detector 218 may be configured to measure signal characteristics on each additional signal channel of the feed structure module 216, as described above. Also, the feed structure module 216 may include a tuner connected to each additional signal channel for controlling the energy delivered by the EM signal, as described above.

Any number of additional signal generator modules 222 may be provided. Further, each additional signal generator module 222 may generate EM radiation at a different frequency to the signal generator module 212 and to each other additional signal generator module 222. For example, the signal generator module 212 may be an RF signal generator module capable of generating RF EM radiation having a frequency of between 100 to 500 kHz. Additionally, a single additional signal generator module 222a may be provided, which may be a microwave signal generator module capable of generating microwave EM radiation having a frequency of 2.45 GHz. However, it is to be understood that an additional signal generator module 222 may generate EM radiation at the same frequency as another additional signal generator module 222 or the signal generator module 214.

In an embodiment, the signal channel for the signal generator module 214 and the signal channel for each additional signal generator module 222 may comprise physically separate signal pathways within the feed structure module 216. Also, the feed structure module 216 may include a signal combining circuit having one or more inputs, wherein each input is connected to a different one of the physically separate signal pathways. Also, the signal combining circuit has an output connected to a common signal pathway for conveying all the EM signals, separately or simultaneously, along a single channel to the output port. Stated differently, the signal combining circuit may provide a junction at which multiple EM signals arrive via separate signal paths from multiple different signal generator modules, and from which all the EM signals leave via the same signal path for delivery to the electrosurgical instrument 204.

In an embodiment, the signal combining circuit includes a switching device 232 for selecting one or more of the EM signals to be connected to the common signal path. The switching device 232 may be controllable based on control commands received from the controller module 212, for example, via a wired link between the controller module 212 and the feed structure module 216. In an embodiment, five additional signal generator modules 222a, 222b, 222c, 222d and 222e are provided in addition to the signal generator module 214 and, as such, a total of six EM signals may be received by the feed structure module 216 and, therefore, the signal combining circuit may have six inputs each delivering a different EM signal to the switching device 232. Based on the control commands, the switching device 232 selects one of the six inputs to connect to the output of the switching device 232. For example, the control commands may specify that the switching device 232 should connect the input from the additional signal generator module 222b to the output such that the EM signal from the additional signal generator module 222b is sent to the electrosurgical instrument 204. Subsequently, the controller module 212 may issue different control commands to the feed structure module 216 which cause the switching device 232 to connect the input from the additional signal generator module 222a to the output such that the EM signal from the additional signal generator 222a is sent to the electrosurgical instrument 204. It is to be understood that selecting one of the inputs for connection to the output means that the other inputs are not connected to the output. However, in an alternative embodiment, more than one input may be selected to be connected to the output such that more than one EM signal is simultaneously sent to the electrosurgical instrument 204.

In summary, the provision of the additional signal generator modules 222a-n in combination with the aforementioned modifications to the feed structure module 216 mean that the electrosurgical system 200 can be adapted to provide different types of EM radiation to treat biological tissue. An advantage of this modular nature is that the functionality of the electrosurgical system 200 can increase so that the system can treat tissue in different ways so as to treat different conditions. Also, the functionality of the electrosurgical system 200 can be reduced so that the system is cheaper or smaller (e.g. more portable).

In an embodiment, each additional signal generator module 222 includes one or more sensors which monitor the operation of different elements of the additional signal generator module 222 and send measurements to the controller module 212. As mentioned above, the controller module 212 (via the watchdog 228) can then compare these measurements to acceptable preset limits and generate an alarm signal if any one of these different elements develops a fault.

The fluid feed module 220 includes a fluid feed structure in fluid communication with a fluid port for outputting fluid to the electrosurgical instrument 204. As seen on FIG. 2, the fluid feed module 220 may be connected to the distal end 205 of the electrosurgical instrument 204 via an instrument fluid feed structure 234. The fluid feed module 220 is controllable by the controller module 212 based on the control commands to supply and control a flow of fluid (e.g. gas or liquid) via the fluid feed structure to the fluid port. For example, the fluid feed module 220 may be connected to the controller module 212 by a wired connection or cable. The purpose of the fluid feed module 220 may be to provide fluid to the distal end 205 of the electrosurgical instrument 204. For example, the fluid may be a gas which is provided to the electrosurgical instrument 204 for generating plasma for treatment of biological tissue. For example, non-thermal plasma may be used to sterilise tissue, for example, to kill bacteria present inside natural orifices or caused by foreign bodies introduced inside the body, i.e. metallic inserts. Also, thermal plasma may be used to cut tissue or perform surface coagulation, for example, for the treatment of ulcers on the surface of the tissue. The electrosurgical instrument 204 may receive gas (from the fluid feed module 220) with either or both of RF energy or microwave energy (from the signal generator module 212 and one or more additional signal generator module 222) and use these components to emit either thermal plasma or non-thermal plasma. For example, for non-thermal plasma, the signal generator module 212 (acting as an RF signal generator module) may generate a high voltage state RF pulse (e.g. 400 V peak for 1 ms) to initiate the plasma using the gas, following which an additional signal generator module 222a (acting as a microwave signal generator module) may generate a microwave pulse for a duration of 10 ms with a duty cycle of 10% and an amplitude of 30 W. On the other hand, for thermal plasma, the duty cycle may be increased to 60% and the amplitude to 60 W. In a general sense, when a flow of gas is present, the RF EM radiation is controllable to strike a conducting gas plasma and the microwave EM radiation is arranged to sustain the gas plasma. In an embodiment, the instrument 204 includes a bipolar probe which strikes the conducting gas between its two conductors. Being able to supply a combination of microwave and RF energy enables a high level of control over the thermal or non-thermal plasma produced at the distal end 205 of the instrument 204, as would be known to the skilled person, for example, in view of WO 2012/076844, which is incorporated herein by reference.

In an embodiment, the fluid feed structure includes a fluid supply (e.g. a canister of compressed air or inert gas, such as argon) which supplies fluid to a fluid controller (e.g. one or more flow switches and/or valves) that operates under instructions received from the controller module 212. The fluid controller may be connected to permit selective delivery of fluid to the fluid port, wherein it may be used in the formation of plasma. The fluid supply system used in the present invention may include the gas control system disclosed in WO 2009/060213, which is incorporated herein by reference.

In an embodiment, the fluid feed module 220 may provide liquid (e.g. saline) to the distal end 205 of the electrosurgical instrument 204. In one embodiment, injection of fluid (saline or the like) is used to plump up the biological tissue at the treatment site. This may be particularly useful where the instrument is used to treat the wall of the bowel or the wall of the esophagus or for protecting the portal vein or the pancreatic duct when a tumour or other abnormality located in close proximity, in order to protect these structures and create a cushion of fluid. Plumping up the tissue in this manner may help to reduce the risk of bowel perforation, damage to the wall of the esophagus or leakage of from the pancreatic duct or damage to the portal vein, etc. This aspect may make it capable of treating other conditions where the abnormality (tumour, growth, lump, etc.) is close to a sensitive biological structure.

Also, the fluid feed module 220 may be configured to receive fluid from the electrosurgical instrument 204. For example, fluid present at a treatment site at the distal end 205 of the instrument 204 may be sucked through the instrument feed structure 234 into the fluid feed module 220, for example, by a pump or other suction device in fluid communication with the fluid feed structure.

In an embodiment, the fluid feed module 220 includes a temperature control element 236 controllable by the controller module 212 based on the control commands to vary a temperature of the fluid flow in the fluid feed structure. In this way, the fluid may be heated or cooled prior to being delivered to the electrosurgical instrument 204. The temperature control element may provide only heating or only cooling. The temperature control element may include a heater for heating the fluid. Also, the temperature control element may include a refrigerator for cooling the fluid.

In an embodiment, the signal generator module 212 (or an additional signal generator module 222) and the fluid feed module 220 may be used together to provide a cryoablation function. For example, the signal generator module 212 may be a microwave signal generator module, and the fluid feed module 220 may be configured to supply a tissue-freezing fluid to the instrument 204. As such, the system 200 is capable of freezing biological tissue in a region around the distal end 205 (e.g. radiating tip) of the instrument 204 and applying microwave energy to the frozen tissue. As water molecules in frozen tissue have reduced vibrational and rotational degrees of freedom compared to non-frozen tissue, less energy is lost to dielectric heating when microwave energy is transmitted through frozen tissue. Thus, by freezing the region around the distal end portion, microwave energy radiated from the distal end portion can be transmitted through the frozen region with low losses and into tissue surrounding the frozen region. This enables the size of the treatment area to be increased compared with conventional microwave ablation instrument (e.g. probes), without having to increase the amount of microwave energy delivered to the distal end portion. Once the tissue surrounding the frozen region has been ablated with microwave energy, the frozen region can be allowed to progressively thaw so that it will dissipate microwave energy and be ablated. The apparatus of the invention also enables various combinations of microwave energy and tissue freezing to be used to effectively ablate biological tissue.

The tissue-freezing fluid may be a cryogenic liquid or gas, and may be referred to herein as a cryogen. The term "cryogen" may refer to a substance which is used to produce temperatures below 0° C. Suitable cryogens include, but are not limited to liquid nitrogen, liquid carbon dioxide and liquid nitrous oxide. The fluid feed structure and instrument fluid feed structure may be provided with a thermal insulation layer made of a thermally insulating material and/or a vacuum jacket to prevent other parts of the apparatus from being cooled by the cryogen. This can also ensure that only tissue in the treatment zone is frozen, and that other parts of the patient which may be in close proximity to the cryogen conveying conduit are not affected by the cryogen.

In an embodiment, the fluid feed module 220 includes one or more sensors which monitor the operation of different elements of the fluid feed module 220 and send measurements to the controller module 212. As mentioned above, the controller module 212 (via the watchdog 228) can then compare these measurements to acceptable preset limits and generate an alarm signal if any one of these different elements develops a fault.

The fluid feed structure 234 is shown in FIG. 2 as being separate from the instrument feed structure 208; however, it is to be understood that in at least some embodiments both 234 and 208 may be contained within the same physical structure, e.g. cable assembly. It may be advantageous to be able to use the same instrument to deliver fluid as delivers RF and/or microwave energy since deflation (e.g. due to fluid seepage or loss of insufflation air) may occur if a separate instrument is introduced into the region or during treatment. The ability to introduce fluid using the same treatment structure enables the level to be topped up as soon as deflation occurs. Moreover, the use of a single instrument to perform desiccation or dissection as well as to introduce fluid also reduces the time taken to perform the overall procedure, reduces the risk of causing harm to the patient and also reduces the risk of infection. More generally, injection of fluid may be used to flush the treatment region, e.g. to remove waste products or removed tissue to provide better visibility when treating. This may be particularly useful in endoscopic procedures. In an embodiment, the feed structures of the invention include those disclosed in WO 2012/095653, which is incorporated herein by reference.

In summary, the embodiment of FIG. 2 illustrates one specific embodiment of the modular system 200, but it can be seen how the functionality of the system 200 can be changed by adding or removing certain optional modules to the core modules. As mentioned above, the core modules are the controller module 212, the signal generator module 214, and the feed structure module 214. These core modules provide mechanisms for controllably generating an EM signal for treating biological tissue, and for delivering that EM signal to an electrosurgical instrument. The EM signal may be any type of electromagnetic signal, such as, RF or microwave. Furthermore, this core functionality can be supplemented in different ways to provide additional functionality. For instance, a signal detector module 218 may be provided to monitor a state of the tissue to determine a tissue characteristic or so that treatment (e.g. the EM signal) can be adapted to the tissue. The signal detector module 218 may use the signal generator module 212 to provide a measurement signal (e.g. a low power microwave signal); however, a separate additional signal generator module 222 may be used to generate the measurement signal. Additionally or alternatively, one or more additional signal generators 222 maybe provided such that the system 200 can deliver EM signals having multiple different frequencies. In one example, both RF and microwave EM signals may be provided by the system 200. In another example, multiple different frequencies of microwave EM signal may be provided. Furthermore the feed structure module 216 can be configured to deliver one or more of the multiple different EM signals separately or simultaneously to the instrument 204. Finally, a fluid feed module 220 may be provided to deliver/receive fluid to/from the treatment site. For example, gas may be provided in combination with RF or microwave energy in order to generate plasma. Alternatively, a tissue freezing fluid may be delivered with EM energy in order to perform cryoablation. Further, liquid may be extracted (e.g. by suction or pumping) from the treatment site.

The system 200 of FIG. 2 includes the remote computing device 206 which communicates wirelessly with the controller module 212. The controller module 212 communicates with each other module of the system 200, and can control each other module of the system via control commands. For example, the controller module 212 may issue a control command to the signal generator module 214 to generate an EM signal. The controller module 212 may issue a control command to the feed structure module 216 to tune the signal channel by varying its adjustable impedance element. In any case, as described above, the controller module 212 may generate the control commands itself but it may also simply forward control commands which it receives from the remote computing device 206. Therefore, in an embodiment, control of the system 200 is centralised in the remote computing device 206, and the controller module 212 may only forward control commands to the modules and may not generate or process data received from the remote computing device 206. However, in another embodiment, the controller module 212 may perform at least some of the control of the system 200 and, as such, control of the system 200 may be shared between the remote computing device 206 and the controller module 212. It is to be understood that in this hybrid arrangement, control of the system 200 may still be centralised in the remote computing device 206, and the controller module 212 may supplement this control only in certain circumstances, for example, when communication between the remote computing device 206 and the controller module 212 breaks down. Alternatively, control of the system 200 may be centralised in the controller module 212, and the remote computing device 206 may supplement this control only in certain circumstances, for example, where user input is required. In summary, therefore, overall control of the system 200 may be controlled by either or both of the remote computing device 206 and the controller module 212.

As mentioned above, the plurality of modules 202 of the system 200 may be housed in a single case or housing. FIG. 9 illustrates a case 250 in accordance with an embodiment. The case 250 may include a plurality of sockets (e.g. slots, holes, orifices) 252a-j, wherein each socket 252a-j is sized and shaped for receiving a different module. For example, the signal generating module 214 is housed in socket 252a, and the feed structure module 216 is housed in socket 252b. Also, sockets 252h-j are empty and, for example, could be filled with further additional signal generator modules 222d, 222e and 222f. In an embodiment, each module is contained within substantially the same sized structure (e.g. case), such that each socket 252a-j is substantially the same size. In an embodiment, each module may be contained in a case with dimensions of 10 cm×2 cm×2 cm. Each socket may include various connectors for connecting a given module into the system 200 as shown in FIG. 2. Some of these connectors may be common to all modules and sockets, such as a power supply connector and a connector to the controller module 212. However, some of these connectors may be specific to a given module, such as, an EM signal connector between the signal generator module 214 (and each additional signal generator module 222) and the feed structure module 216. In any case the location of at least some connectors may be standardised in the sockets and the modules. For example, the power supply connector may be located in the same place for each socket and module.

In an embodiment, one or more core modules may be housed within the casing in a fixed manner, i.e. not removably contained within a socket. For example, the controller module 212 may be contained within an internal cavity of the case (as represented in FIG. 9 by the dashed lines). The internal cavity may be accessible via a hatch or opening (not shown).

In an embodiment, the case 250 includes two connectors 254 and 256. The connector 254 may provide a mechanism by which the instrument feed structure 208 connects with the feed structure module 216. The connector 256 may provide a mechanism by which the instrument fluid feed structure 234 connects with the fluid feed module 220. In an embodiment, the two connectors 254 and 256 are contained within the same physical connector.

In an embodiment, the case 250 include a connector 258 for connecting the case 250 to a power supply, such as a mains supply. For example, the connector 258 may provide a mechanism by which each module is fed power from the mains supply.

It is to be understood that whilst FIG. 9 illustrates that the case 250 has ten sockets, in some other embodiments, more or less than ten sockets may be provided. Also, whilst the controller module 212 is shown within an internal cavity of the case 250, in some other embodiments the controller module 212 may be included in a socket. Also, whilst the sockets are shown as being rectangular, the sockets could be any shape which can receive a module. Additionally, the case is shown as generally rectangular but could be any shape.

The embodiment of FIG. 2 illustrates a system 200 in which a plurality of modules 202 can be interconnected in different ways to provide different electrosurgical capabilities. Whilst many different configurations are possible, each module must communicate with the remote computing device 206 via the controller module 212. Stated differently, only the controller module 212 includes a wireless communication interface and is capable of communicating wirelessly with the remote computing device 206.

FIGS. 3 to 6 illustrate an alternative modular electrosurgical system 300 in which each module includes a controller which can independently wirelessly communicate with a remote computing device. As such, control of the plurality of modules must be centralised in the remoted computing device. However, other than this distinction, the system 300 is similar to the system 200. A description of the system 300 now follows which focusses on aspects of the system 300 which are different to the system 200. Unless otherwise stated, the function and operation of the system 300 is analogous to that of the system 200 described above.

Figure 3:
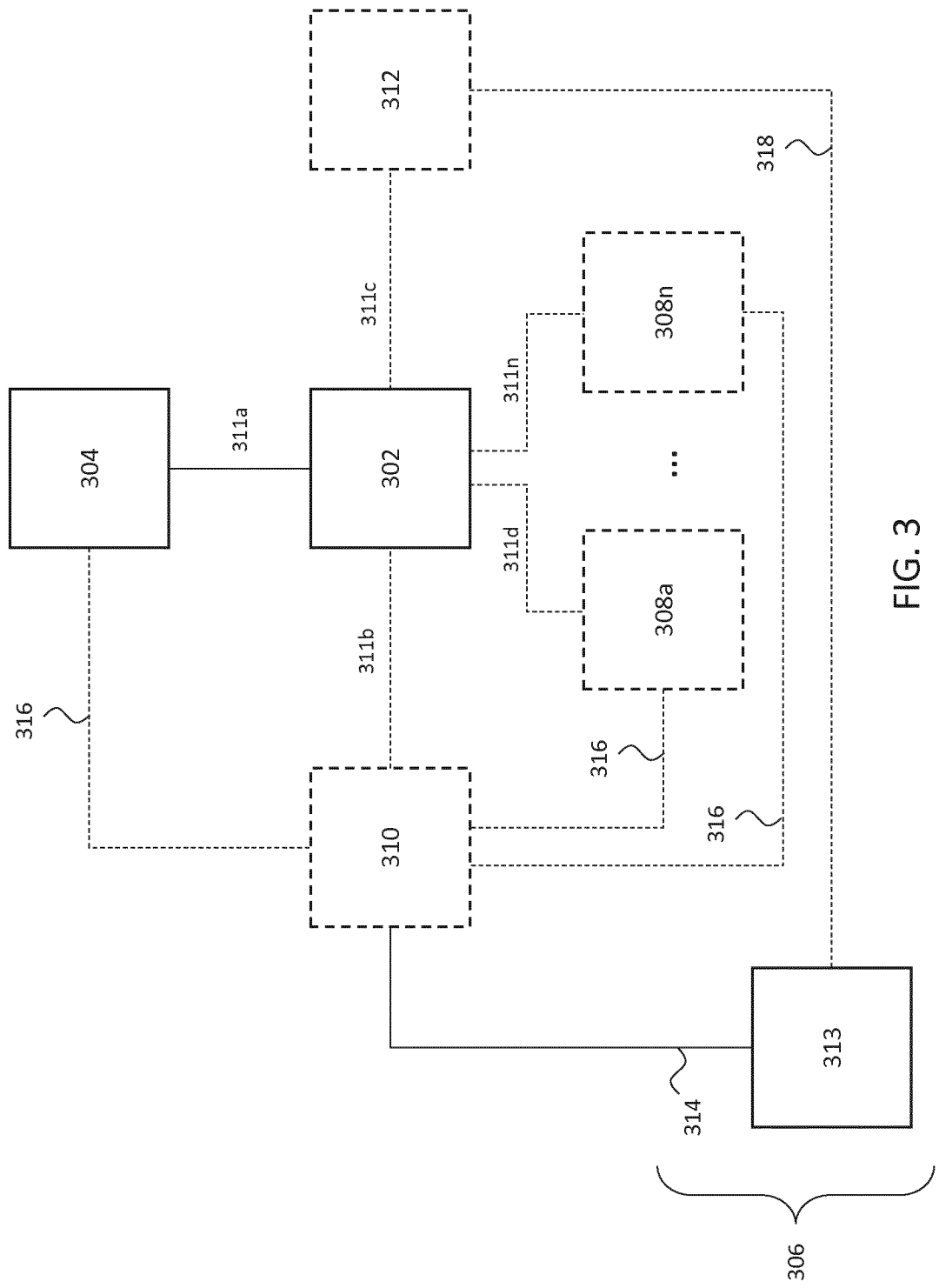
FIG. 3 is a schematic diagram of a modular electrosurgical system, in accordance with another embodiment.

As seen in FIG. 3, the modular electrosurgical system 300 includes: a remote computing device 302, a signal generator module 304, and an electrosurgical instrument 306. The signal generator module 304 may be considered as the core module, however, the system 300 may include other optional modules. The optional modules include: one or more additional signal generator modules 308a-n, a signal combining module 310, and a fluid feed module 312. Optional features of FIGS. 3 to 6 are indicated by dashed lines. The various connections between the different elements of system 300 are shown in FIG. 3. For example, each of the modules separately communicates with the remote computing device 302, for example, via an independent wireless communication channel 311a-n. The signal generator module 304 is also coupled to the electrosurgical instrument 306 so as to provide an EM signal thereto. Where no additional signal generator modules 308a-n are present, no signal combiner module 310 may be present and, therefore, the signal generator module 304 may be directly connected to a distal end (or distal assembly) 313 of the electrosurgical instrument 306 by an instrument feed structure 314 of the electrosurgical instrument 306. Alternatively, where at least one additional signal generator module 308a-n is present, the signal combiner module 310 may be required, and both the signal generator module 304 and the at least one additional signal generator module 308 are coupled to the electrosurgical instrument 306 via the signal combiner module 310. The signal generator module 304 and each additional signal generator module 308 may be connected to the signal combiner module 310 by a combiner feed structure 316 for conveying EM radiation, such as a cable, whereas the signal combiner module 310 may be connected to the instrument feed structure 314. Furthermore, when present, the fluid feed module 312 is connected to the electrosurgical instrument via an instrument fluid feed structure 318. FIG. 3 shows the fluid feed structure 318 as being separate from the instrument feed structure 314; however, it is to be understood that in at least some embodiments both 318 and 314 may be contained within the same physical structure, e.g. cable assembly.

Each of the modules 304, 308, 310 and 312 will now be described in turn with reference to FIGS. 4 to 6.

Figure 4:
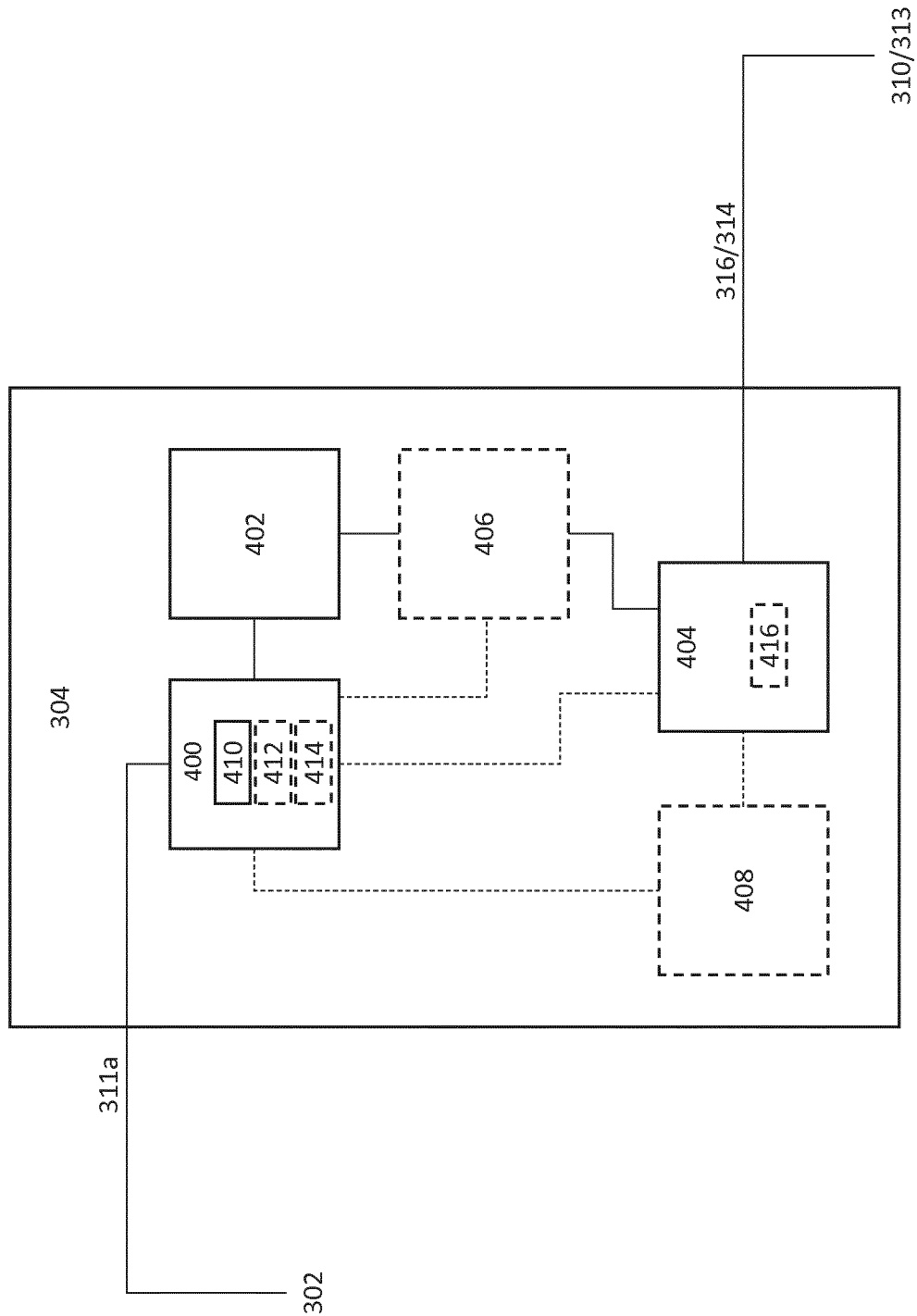
FIG. 4 is a schematic diagram of a signal generator module of the modular electrosurgical system of FIG. 3.

As seen on FIG. 4, the signal generator module 304 includes a controller 400, a signal generator 402, and a feed structure 404. These are considered as the core elements of the signal generator module 304. Additionally, however, the signal generator module 304 may include the following optional elements: a pulse generator 406 and a signal detector 408. The various connections between these elements is shown in FIG. 4. It is noted that when the pulse generator 406 is absent, the signal generator 402 is coupled directly to the feed structure 404, but when the pulse generator 406 is present, the signal generator 402 is coupled to the feed structure 404 via the pulse generator 406.

The controller 400 includes a wireless communication interface 410 which is operable to wirelessly communicate with the remote computing device 302 so as to receive instructions therefrom. Further, the controller 400 is operable to provide control commands based on the received instructions. As such, the controller 400 is analogous to the controller module 212 of FIG. 2. For example, the controller 400 may forward control commands from the remote computing device 302 to the signal generator 402, or the controller 400 may generate control commands for the signal generator 402 based on data received from the remote computing device 302. Also, communication between the signal generator module 304 and the remoted computing device 302 may be two-way, such that the control commands generated by the controller 400 can be sent from the controller 400 to the remote computing device 302. Similarly to the controller module 212, the controller 400 may include a processor 412 and a watchdog 414 which operate in an analogous manner to the processor 226 and the watchdog 228 of FIG. 2.

The signal generator 402 is in communication with the controller 400 so as to receive the control commands. The signal generator 402 is then operable to generate and control EM radiation based on the control commands to form an EM signal. The operation of the signal generator 402 is analogous to the operation of the signal generator module 214 of FIG. 2. For example, the control commands may instruct the signal generator 402 to turn ON, or turn OFF, or turn ON for a particular duration, or to provide EM radiation at a particular power (or amplitude).

The feed structure 404 is for conveying the EM signal which is generated by the signal generator 402. Specifically, the feed structure 404 includes an output port for outputting the EM signal to the electrosurgical instrument 306, and the feed structure 404 includes a signal channel for connecting the signal generator 402 to the output port. The feed structure 404 is analogous to the feed structure module 216 of FIG. 2.

When present, the optional pulse generator 406 is positioned in between the signal generator 402 and the feed structure 404. The pulse generator 406 is analogous to the pulse generator 229 of FIG. 2 and, as such, the pulse generator 406 is controllable by the controller 400 based on control commands to generate pulsed EM radiation from the EM radiation which is output from the signal generator 402. For example, the EM radiation which is generated and controlled by the signal generator module 402 is operated on by the pulse generator 406 so as to generate pulsed EM radiation which then forms the EM signal which is received by the feed structure 404. In this way, the signal generator module 304 is modified so as to provide a pulsed EM signal, for example, for electroporation.

When present, the optional signal detector 408 is coupled to the feed structure 404 so as to sample a signal characteristic on the signal channel of the feed structure 404, and to generate a detection signal which is indicative of the signal characteristic. As such, the signal detector 408 is analogous to the signal detector module 218 of FIG. 2. That is, example signal characteristics may include: a voltage, a current, a forward power, or a reflected power. In an embodiment, the signal generator 402 may be configured to deliver a low power EM signal for the purposes of signal detection, and this low power signal may be referred to as a measurement signal, since it is generated for the purposes of measuring biological tissue at the distal end 313 of the electrosurgical instrument 306. Alternatively, an additional signal generator module 308a-n may be used to provide the measurement signal.

In an embodiment, the controller 400 is in communication with the signal detector 408 so as to receive the detection signal. Also, the controller 400 is operable to generate the control commands based on the detection signal. Additionally or alternatively, the controller 400 is operable to transmit the detection signal from the wireless communication interface 410 to the remote computing device 302. As such, the remote computing device 302 can be responsible for generating control commands based on the detection signal, and then sending those control commands to the controller 400 for forwarding to the signal generator 402.

In an embodiment, the feed structure 404 further comprises a tuner 416 connected to the signal channel for controlling the energy delivered by the EM signal. The tuner 416 includes an adjustable impedance element that is controllable by the controller 400 based on the detection signal. The tuner 416 is analogous to the tuner 230 of FIG. 2 and, as such, may function to promote efficient transfer of EM radiation into tissue. For example, information detected from the signal channel may be used to determine the adjustment of the adjustable impedance element on the signal channel to provide dynamic power matching between the electrosurgical instrument 306 and the tissue, which ensures efficient and controllable energy transfer between the electrosurgical system 300 and the biological tissue.

In an embodiment, the controller 400 is connected to each other element of the signal generator module 304 via a separate wired connection, such as, a cable.

When the system 300 includes one or more additional signal generator modules 308a-n, each of the additional signal generator modules 308a-n is analogous to the signal generator module 304 described above with reference to FIG. 4. Each of the additional signal generator modules 308a-n is also analogous to one of the additional signal generator modules 222a-n of FIG. 2. Any number of additional signal generator modules 308a-n may be provided. Further, each of the additional signal generator modules 308a-n may generate EM radiation at a different frequency to the signal generator module 304 and to each other additional signal generator module. However, it is to be understood that one of the additional signal generator modules 308a-n may generate EM radiation at the same frequency as another additional signal generator module or the signal generator module 304. In any case, the remote computing device 302 functions to control operation of each of the different signal generator modules. As such, the remote computing device 302 can selectively control each signal generator module.

It is to be understood that the signal channel of the feed structure 404 of the signal generator module 304 is a physically separate signal pathway to the corresponding signal channel of the feed structure of each of the additional signal generator modules 308a-n. As such, the signal combining module 310 provides a mechanism for combining together the EM signal from the signal generator module 304 and the EM signal from each of the additional signal generator modules 308a-n for delivery to the electrosurgical instrument 306.

Figure 5:
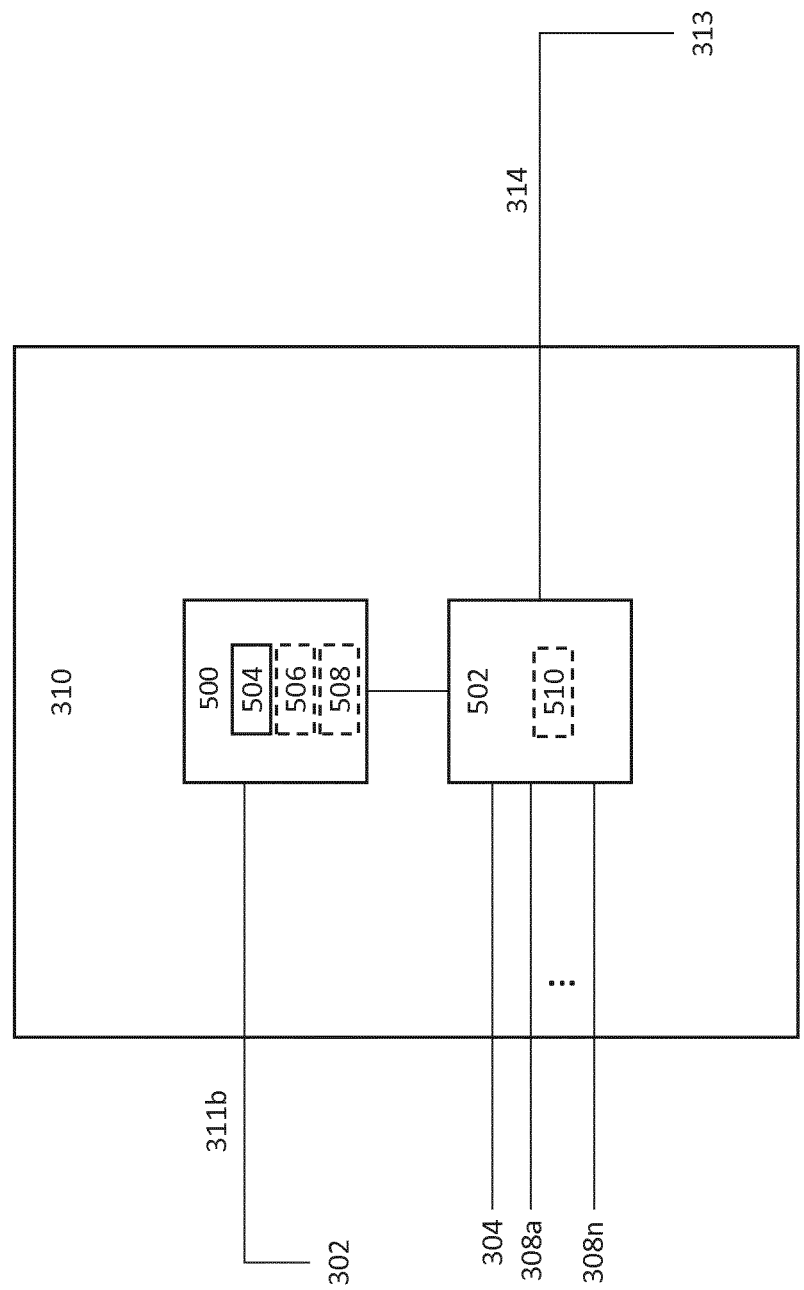
FIG. 5 is a schematic diagram of a fluid feed module of the modular electrosurgical system of FIG. 3.
Figure 6:
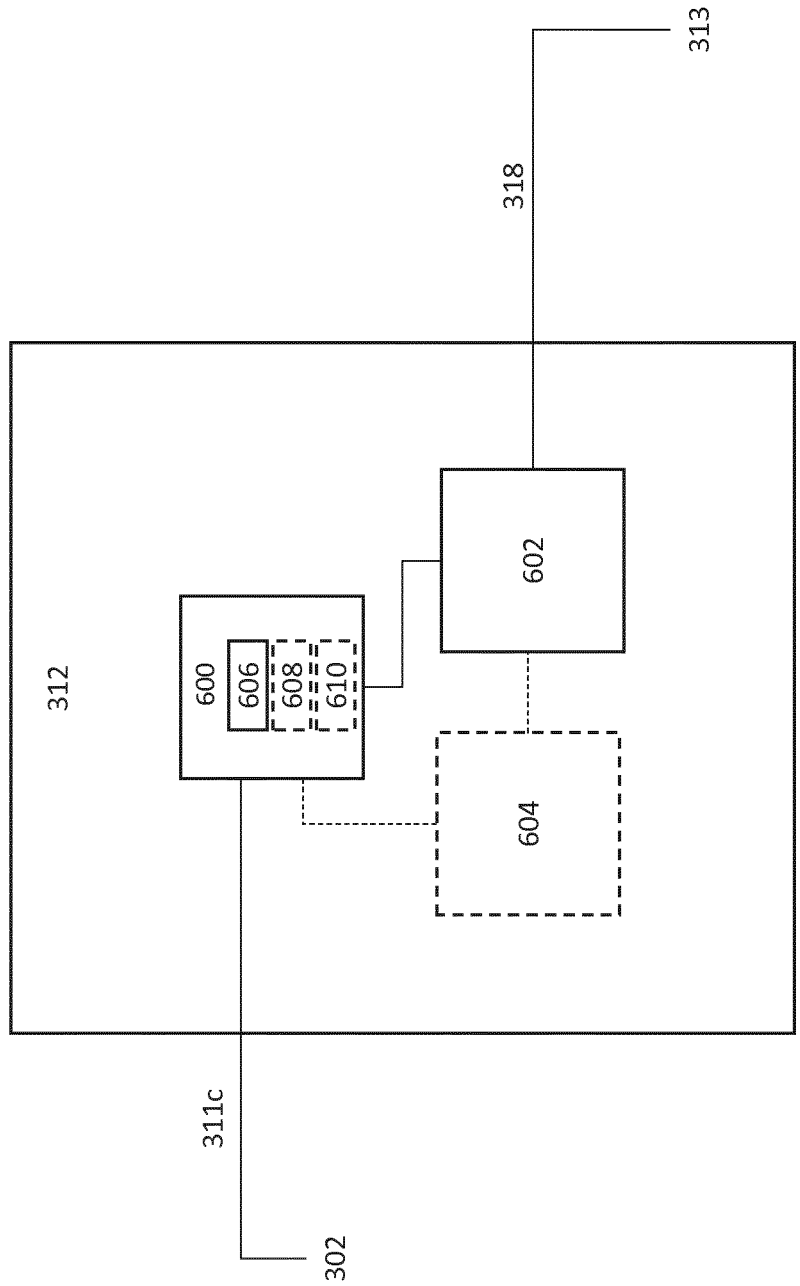
FIG. 6 is a schematic diagram of a signal combining module of the modular electrosurgical system of FIG. 3.

As seen on FIG. 5, the signal combiner module 310 includes a controller 500 and a feed structure 502. The controller 500 is in communication with the feed structure 502 (e.g. via a wired connection or cable) so as to control operation of the feed structure 502 via control commands. Specifically, the controller 500 has a wireless communication interface 502 operable to wirelessly communicate with the remote computing device 302 so as to receive instructions therefrom. The controller 500 is operable to provide control commands based on the received instructions. For example, the controller 500 may forward control commands from the remote computing device 302 to the feed structure 502, or the controller 500 may generate control commands for the feed structure 502 based on data received from the remote computing device 302. Similarly to the controller module 212, the controller 500 may include a processor 506 and a watchdog 508 which operate in an analogous manner to the processor 226 and the watchdog 228 of FIG. 2.

Additionally, the signal combiner module 310 includes a plurality of input ports for receiving a plurality of input EM signals. Each input port is for receiving a separate EM signal from either the signal generator module 304 or a different one of the additional signal generator modules 308a-n. Further, the signal combining module 310 includes an output port for transmitting an output EM signal to the electrosurgical instrument 306. As such, the signal combining module 310 provides a mechanism for combining together multiple EM signals for delivery to a single electrosurgical instrument 306. Furthermore, the feed structure 502 may include a switching device 510, and the feed structure 502 includes a plurality of separate signal pathways coupled to the plurality of input ports for conveying the plurality of input EM signals to the switching device 510. Also, the feed structure 502 has a common signal pathway connected to the output port, and the switching device 510 is configured to selectively connect one or more of the plurality of separate signal pathways to the common signal pathway based on the control commands which the feed structure 502 receives from the controller 500. As such, the signal combiner module 310 is analogous to the feed structure module 216 of FIG. 2.

When the system 300 includes the fluid feed module 312, the fluid feed module 312 includes a controller 600 in communication with a fluid feed structure 602. Additionally, an optional temperature control element 604 may be provided which is in communication with both the controller 600 and the fluid feed structure 602. The controller 600 may be connected to the fluid feed structure 602 and the temperature control element 604 via separate wired connections or cables. The controller 600 has a wireless communication interface 602 operable to wirelessly communicate with the remote computing device 302 so as to receive instructions therefrom. The controller 600 is operable to provide control commands based on the received instructions. For example, the controller 600 may forward control commands from the remote computing device 302 to the fluid feed structure 602 and the temperature control element 604, or the controller 600 may generate control commands for the fluid feed structure 602 and the temperature control element 604 based on data received from the remote computing device 302. Similarly to the controller module 212, the controller 600 may include a processor 608 and a watchdog 610 which operate in an analogous manner to the processor 226 and the watchdog 228 of FIG. 2.

The fluid feed structure 602 has a fluid port for outputting fluid to the electrosurgical instrument 306. As seen on FIG. 3, the fluid feed module 312 may be connected to the distal end 313 of the electrosurgical instrument 306 via an instrument fluid feed structure 318. The fluid feed structure 602 is controllable by the controller 600 based on the control commands to supply and control a flow of fluid (e.g. gas or liquid) via the fluid feed structure 602 to the fluid port. The purpose of the fluid feed module 312 may be to provide fluid (e.g. gas or liquid) to the distal end 313 of the electrosurgical instrument 306. For example, the fluid may be a gas which is provided to the electrosurgical instrument 306 for generating plasma for treatment of biological tissue. Also, the fluid feed structure 602 may include a pump or other suction device for extracting fluid (e.g. liquid) from the treatment site. As such, the fluid feed module 312 is analogous to the fluid feed module 220 described above with reference to FIG. 2.

When present, the temperature control element 604 is controllable by the controller 600 based on control commands to vary a temperature of the fluid flow in the fluid feed structure 602. In this way, the fluid may be heated or cooled prior to being delivered to the electrosurgical instrument 306. The temperature control element 604 may provide only heating or only cooling of the fluid. As such, temperature control element 604 is analogous to the temperature control element 236 described above with reference to FIG. 2.

In an embodiment, the signal generator 304 and the fluid feed module 312 may be used together to provide a cryoablation function, in an analogous manner to as described above with reference to the signal generator module 214 and the fluid feed module 220 of FIG. 2.

It is to be understood that a module of the system 300 may include one or more sensors which monitor the operation of different elements of the module, and send measurements to the controller of the module. As mentioned above, the controller (via its watchdog) can then compare these measurements to acceptable limits and generate an alarm signal if any one of these different elements develops a fault. The alarm signal maybe transmitted via the controller's wireless communication interface to the remote computing device 302. The controller and/or the remote computing device 302 may generate control commands to control the system to handle the fault, for example, by shutting down. In an embodiment, each module includes one or more sensors which operate in this manner to facilitate fault detection and handling. In this way, the system 300 is analogous to the system 200 of FIG. 2.

In summary, the embodiment of FIGS. 3 to 6 illustrates one specific embodiment of the modular system 300, but it can be seen how the functionality of the system 300 can be changed by adding or removing certain optional modules. As mentioned above, the core module of the system 300 is the signal generator module 304. This core module provides a mechanism for controllably generating an EM signal for treating biological tissue, and for delivering that EM signal to an electrosurgical instrument. The EM signal may be any type of electromagnetic signal, such as, RF or microwave. Furthermore, this core functionality can be supplemented in different ways to provide new functionality. For instance, a signal detector 408 may be added to the signal generator module 304 to monitor a state of the tissue so that treatment can be adapted to the tissue. Additionally or alternatively, one or more additional signal generators modules 308 maybe provided such that the system 300 can deliver EM signals having multiple different frequencies. In one example, both RF and microwave EM signals may be provided by the system 300. In another example, multiple different frequencies of microwave EM signal may be provided. Furthermore, a signal combining module 310 can be added to control delivery of one or more of the multiple different EM signal separately or simultaneously to the instrument 306. Finally, a fluid feed module 312 may be provide to deliver/extract fluid to/from the treatment site. For example, gas may be provided in combination with RF or microwave energy in order to generate plasma. Alternatively, a tissue-freezing fluid may be delivered with microwave energy in order to perform cryoablation. Further, liquid may be extracted (e.g. by suction or pumping) from the treatment site.

The system 300 of FIGS. 3 to 6 includes the remote computing device 302 which wirelessly communicates with each module 304, 308*a-n*, 310 and 312. The remote computing device 302 can control each module (304, 308*a-n*, 310 and 312) of the system 300 via control commands. For example, the remote computing device 302 may issue a control command to the signal generator module 304 to generate an EM signal. Also, the remote computing device 302 may issue a control command to the fluid feed module 312 to generate a fluid flow. Alternatively, as described above, each module (304, 308*a-n*, 310 and 312) includes a controller which may generate the control commands itself based on data received from the remote computing device 302. Therefore, in an embodiment, control of the system 300 may be centralised in the remote computing device 302 and the controllers of the various modules may only act on control commands received from the remote computing device 302. However, in another embodiment, the controller of each module may perform at least some of the control of its respective module and, as such, control of the system 300 may be shared between the remote computing device 206 and each module (304, 308*a-n*, 310 and 312). It is to be understood that in this hybrid arrangement, control of the system 300 may still be centralised in the remote computing device 206, and the controllers of the various modules may supplement this control only in certain circumstances, for example, when communication between the remote computing device 206 and one or more modules breaks down. In summary, therefore, overall control of the system 300 may be centralised in the remote computing device 206 but may be supplemented by the individual controllers of the various modules.

The above-described modular system 200 includes the remote computing device 206, and the above-described modular system 300 includes the remote computing device 302. Both the remote computing devices 206 and 302 may be described, generally, as a computing device having: at least one processor, and at least one memory including computer program code. In use, the least one memory and the computer program code are configured to, with the at least one processor, cause the remote computing device to perform various operations which enable at least some of the system functionality described above with reference to FIGS. 2 to 6.

A detailed example remote computing device is described below with reference to FIG. 7. In an embodiment, the remote computing devices 206 and 302 are the remote computing device of FIG. 7.

FIG. 7 is a schematic of a wireless computing device 1100. The following description of the wireless computing device 1100 is provided by way of example only and is not intended to be limiting.

The wireless device 1100 comprises a keypad 1102, a touch-screen 1104, a microphone 1106, a speaker 1108 and an antenna 1110. The wireless device 1100 is capable of being operated by a user to perform a variety of different functions, such as, for example, hosting a telephone call, sending an SMS message, browsing the Internet, sending an email, and providing satellite navigation.

The wireless device 1100 comprises hardware to perform communication functions (e.g. telephony, data communication), together with an application processor and corresponding support hardware to enable the wireless device 1100 to have other functions, such as, messaging, Internet browsing, email functions and the like. The communication hardware is represented by the RF processor 1112 which provides an RF signal to the antenna 1110 for the transmission of data signals, and the receipt therefrom. Additionally provided is a baseband processor 1114, which provides signals to and receives signals from the RF Processor 1112. The baseband processor 1114 also interacts with a subscriber identity module 1116, as is well known in the art. The communication subsystem enables the wireless device 1100 to communicate via a number of different communication protocols including 3G, 4G, 5G, GSM, WiFi, Bluetooth™ and/or CDMA. The communication subsystem of the wireless device 1100 is beyond the scope of the present invention.

The keypad 1102 and the touch-screen 1104 are controlled by an application processor 1118. A power and audio controller 1120 is provided to supply power from a battery 1122 to the communication subsystem, the application processor 1118, and the other hardware. The power and audio controller 1120 also controls input from the microphone 1106, and audio output via the speaker 1108. Also provided is a global positioning system (GPS) antenna and associated receiver element 1124 which is controlled by the application processor 1118 and is capable of receiving a GPS signal for use with a satellite navigation functionality of the wireless device 1100.

In order for the application processor 1118 to operate, various different types of memory are provided. Firstly, the wireless device 1100 includes Random Access Memory (RAM) 1126 connected to the application processor 1118 into which data and program code can be written and read from at will. Code placed anywhere in RAM 1126 can be executed by the application processor 1118 from the RAM 1126. RAM 1126 represents a volatile memory of the wireless device 1100.

Secondly, the wireless device 1100 is provided with a long-term storage 1128 connected to the application processor 1118. The long-term storage 1128 comprises three partitions, an operating system (OS) partition 930, a system partition 1132 and a user partition 1134 The long-term storage 1128 represents a non-volatile memory of the wireless device 1100.

In the present example, the OS partition 1130 contains the firmware of the wireless device 1100 which includes an operating system. Other computer programs may also be stored on the long-term storage 1128, such as application programs, and the like. In particular, application programs which are mandatory to the wireless device 1100, such as, in the case of a smartphone, communications applications and the like are typically stored in the system partition 1132. The application programs stored on the system partition 1132 would typically be those which are bundled with the wireless device 1100 by the device manufacturer when the wireless device 1100 is first sold.

Application programs which are added to the wireless device 1100 by the user would usually be stored in the user partition 1134.

As stated, the representation of FIG. 7 is schematic. In practice, the various functional components illustrated may be substituted into one and the same component. For example, the long-term storage 1128 may comprise NAND flash, NOR flash, a hard disk drive or a combination of these. Additionally, one or more components maybe omitted.

In a general sense, regardless of the hardware construction of the remote computing devices 206 and 302, both remote computing devices provide a mechanism by which a user (e.g. a human operator) can interface with the modular systems 200 and 300. For example, the user can issue instructions via the remote computing devices 206 and 302 to configure or enable functionality of the systems 200 or 300, such as, delivering an EM signal or fluid to biological tissue. Additionally, the user can receive feedback from the systems 200 or 300 via the remote computing devices 206 and 302, such as, error notifications or data on a particular surgical procedure (e.g. control commands or a detection signal). Additionally, the remote computing devices 206 and 302 provide a mechanism by which the feedback data can be stored, displayed, manipulated or used in controlling further electrosurgical procedures. In an embodiment, the remote computing device displays a user interface on its touch-screen for both the receipt of input from the user and the delivery of content (e.g. graphs, tables, warnings, updates, etc.) to the user. The user interface may be mechanism by which all modules can be controlled and monitored.

A detailed embodiment of the operation of the remote computing device 206 of system 200 will now be described with reference to the flow diagram 1200 of FIG. 8, to illustrate some of the above-described functionality of the system 200.

Processing begins at block 1202, in which the remote computing device 206 generates input data based on a user input. For example, in the case of the system 200, the remote computing device 206 may include a touch-screen display which the user controls to provide the user input. The input data may specify one or more operating parameters of one or more modules of the system 200, such as, the signal generator module 212. For example, the user input may be provided to cause the remote computing device 206 to activate the signal generator module 214 to generate an EM signal for delivery to the instrument 204. As such, the operating parameters may include an instruction for the controller module 212 to "turn ON" the signal generator module 214.

At block 1204, the remote computing device 206 generates a data packet for wireless transmission to the controller module 212. The data packet includes the operating parameters which were input by the user. The data packet is generated such that the operating parameters can be wirelessly transmitted to the controller module 212. For example, the operating parameters may be combined with communication parameters, such as, a source address and destination address, which enables wireless communication of operating parameters to the controller module 212. Additionally, the remote computing device 206 may encrypt the operating parameters such that the data packet includes encrypted operating parameters for added security and safety.

At block 1206, the data packet is wirelessly transmitted from the remote computing device 206 to the controller module 212 via the wireless communication channel 210. The wireless communication channel 210 may be a direct (e.g. dedicated) path between the remote computing device 206 and the controller module 212, or the wireless communication channel 210 may include one or more other computing devices or networks, such as, the Internet, one or more wireless area networks, and/or one or more local area networks.

On receipt of the data packet, the controller module 212 extracts the operating parameters and generates corresponding control commands, as described above. For example, the control commands instruct the signal generator module 214 to generate the EM signal.

It is to be understood that the operating parameters are not limited to turning ON the signal generator module 214. For example, the operating parameters may include other instructions for the signal generator module 214, such as, to turn OFF the EM signal, to turn ON the EM signal for a specific duration, to generate an EM signal with a particular power (or amplitude), generate a pulsed EM signal having particular pulse characteristics (e.g. pulse width, duty cycle, amplitude, etc.) Additionally, the operating parameters may include instructions for modules other than the signal generator module 214. For example, where the operating parameters are for an additional signal generator module 222, they may be analogous to those described with reference to the signal generator module 214. Where the operating parameters are for the fluid feed module 220, they may specify that a gas supply be turned ON, or that the temperature control element set the gas to a particular temperature. Where the operating parameters are for the feed structure 216, they may specify that an EM signal from one or more particular signal generator modules be delivered to the instrument 204. In any case, control commands including the operating parameters (or control commands generated based on the operating parameters) are delivered to the relevant module by the controller module 212.

At block 1208, the remote computing device 206 receives a data packet from the controller module 212, via the wireless communication channel 210.

At block 1210, the remote computing device 206 extracts data from the received data packet. Where the controller module 212 has encrypted the data, the remote computing device must decrypt the data using a corresponding decryption protocol in order to extract the data. Alternatively, where the data is not encrypted, the data may be extracted by removing parts of the data packet which are no longer required, for example, communication parameters (e.g. headers or addresses).

At block 1212, the remote computing device 206 processes the extracted data. The nature of the processing will depend on the extracted data, but generally it provides a mechanism to provide the user with real-time feedback and monitoring on the operation of the system 200. For example, possible processing operations include: storing the data, and displaying the data (e.g. in graphs, charts or tables) on a display screen of the remote computing device 206. Further, the remote computing device 206 may manipulate the data and, possibly, use the data to synthesize further data. In an example, the extracted data may include an alarm signal from the controller module 212 which notifies that an element of the signal generator module 214 is recording a temperature outside of preset limits. In this case, the remote computing device 206 may generate data (e.g. operating parameters) for transmission to the controller module 212 which causes the controller module 212 to issue control commands to the signal generator module 214 to cause the signal generator module 214 to shut down. Alternatively, the extracted data may include a detection signal from the signal detector module 218, and the remote computing device 206 may generate data (e.g. operating parameters) for transmission to the controller module 212 which causes the controller module 212 to issue control commands to the signal generator module 214 to cause the signal generator module 214 to adjust the tuner 230 so as to improve the efficiency of the transfer of EM radiation into tissue at a treatment site at the distal end 205 of the electrosurgical instrument 204. It is also to be understood that block 1212 may involve multiple different processing operations. For instance, considering the above example relating to overheating, the remote computing device 206 may: (i) generate a data entry for storage which includes the offending temperature with other data identifying the current operating session; (ii) store the data entry in a memory of the remoted computing device 206; (iii) display a warning on a display screen of the remote computing device 206 to warn the user of the fault; (iv) generate a data packet for transmission to the controller module 212 which includes data to cause the controller module 212 to issue control commands to the signal generator module 214 to cause the signal generator module 214 to shut down; and, (v) transmit the data packet to the controller module 212.

In addition to the above, the remote computing device 206 provides a mechanism by which session data (i.e. data relating to a particular surgical procedure) of the system 200 can be saved, recalled, displayed, exported, printed, and linked with data on other computing devices or systems (e.g. a hospital patent database). For example, data collected from the system 200 during a patient's operation may be stored in association with that patient's entry in the hospital's patient database. Additionally, the remote computing device 206 may collect data from the system 200 so as to enable data analytics relating to electrosurgical procedures. For example, session data may be stored with a procedure outcome, and machine learning, artificial intelligence or pattern matching may be performed by the remote computing device 206 to predict an outcome of future procedures based on new session data. Additionally or alternatively, the remoted computing device 206 may transmit session data and outcome data to a global repository such a cloud stored database. In this way, the remote computing device 206 may be able to access session data and outcome data from other remote computing devices 206 such that its outcome predictions are more accurate.

Whilst the above description of the operation of the remote computing device has been presented in connection with the modular system 200, it is to be understood that the description applies equally to the module system 300. However, it is to be understood that the remote computing device 302 is capable of communicating (e.g. transmitting and receiving data packets) separately with each of: the signal generator module 304, each additional signal generator module 308, the signal combining module 310, and the fluid feed module 312. Therefore, the data sent to each module should relate to the functionality of that module. For example, the remote computing device 302 might send a data packet to the signal generator module 304 which relates to generating an EM signal. However, the remote computing device 302 might not send a data packet to the signal generator module 304 which relates to generating a gas flow—since this data packet should instead be sent directly to the fluid feed module 312.

It is to be understood that modules from the system 300 may be included into the system 200 so as to form a combined embodiment which is centrally controlled by the remote computing device. For example, the combined system may include the remote computing device 206, the electrosurgical instrument 204 and the core modules of system 200, i.e. the controller module 212, the signal generator module 214 and the feed structure module 216. Additionally, the system 200 may include the fluid feed module 312 which interfaces with the electrosurgical instrument 204 via instrument fluid feed structure 318. The remote computing device 206 may control the combined system by issuing control commands to the controller module 212 for the signal generator module 214 and the feed structure module 216; however, the remote computing device 206 may issue control commands directly to the fluid feed structure 318 (i.e. not via the controller module 212).

It is to be understood that various embodiments of the invention may be particularly suitable in gastrointestinal (GI) procedures associated with the lower and upper GI tract, e.g. to remove polyps on the bowel, i.e. for endoscopic mucosal resection, or endoscopic submucosal dissection. The invention may also lend itself to other procedures, e.g. in general surgery or laparoscopic surgery. The invention may find use in ear, nose and throat procedures and liver resection. The invention may also be used to address procedures associated with the pancreas, e.g. to resect or remove tumours or abnormalities in close proximity to the portal vein or the pancreatic duct.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the words "have", "comprise", and "include", and variations such as "having", "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means, for example, +/−10%.

The words "preferred" and "preferably" are used herein refer to embodiments of the invention that may provide certain benefits under some circumstances. It is to be appreciated, however, that other embodiments may also be preferred under the same or different circumstances. The recitation of one or more preferred embodiments therefore does not mean or imply that other embodiments are not useful, and is not intended to exclude other embodiments from the scope of the disclosure, or from the scope of the claims.

The invention claimed is:

1. A modular electrosurgical system comprising:
a remote computing device having at least one processor and at least one memory including computer program code;
a controller module having a wireless communication interface operable to wirelessly communicate with the remote computing device so as to receive data therefrom, the controller module being operable to provide control commands based on the received data;
a signal generator module in communication with the controller module so as to receive the control commands, the signal generator module operable to generate and control electromagnetic (EM) radiation based on the control commands to form an EM signal; and
a feed structure module for conveying the EM signal and having an output port for outputting the EM signal to an electrosurgical instrument, the feed structure having a signal channel for connecting the signal generator module to the output port;
wherein the at least one memory and the computer program code are configured to, with the at least one processor, cause the remote computing device at least to:
generate input data based on user input, the input data specifying at least one operating parameter of the signal generator module;
generate a data packet for wireless transmission to the controller module, the data packet including the at least one operating parameter; and
transmit the data packet to the controller module via a wireless communication channel;
wherein the control commands are based on the at least one operating parameter of the data packet received by the controller module.

2. The system of claim 1, wherein the controller module further comprises a processor in communication with the wireless communication interface so as to receive the received data, the processor being operable to generate the control commands based on the received data.

3. The system of claim 2, wherein the controller module is operable to transmit the control commands via the wireless communication interface to the remote computing device.

4. The system of claim 1, wherein the controller module is operable to decrypt data received at the wireless communication interface, and to encrypt data transmitted from the wireless communication interface.

5. The system of claim 1, wherein the controller module comprises a watchdog for monitoring a potential error condition of the system, the watchdog being operable to generate an alarm signal when the error condition occurs.

6. The system of claim 5, further comprising a sensor operable to monitor operation of part of the system and to generate corresponding sensor data, and wherein the watchdog is operable to generate the alarm signal based on a comparison between the sensor data and one or more sensor thresholds.

7. The system of claim 5, wherein the controller module is operable to transmit the alarm signal via the wireless communication interface to the remote computing device.

8. The system of claim 5, wherein the watchdog is operable to generate the alarm signal when the wireless communication interface loses communication with the remote computing device for at least a preset time period.

9. The system of claim 5, wherein the controller module is operable to generate the control commands based on the alarm signal.

10. The system of claim 1, further comprising a signal detector module coupled to the signal channel so as to sample a signal characteristic on the signal channel and to generate therefrom a detection signal indicative of the signal characteristic.

11. The system of claim 10, wherein the controller module is operable to generate the control commands based on the detection signal.

12. The system of claim 10, wherein the controller module is operable to transmit the detection signal via the wireless communication interface to the remote computing device.

13. The system of claim 10, wherein the feed structure module further comprises a tuner connected to the signal channel for controlling energy delivered by the EM signal, the tuner comprising an adjustable impedance element that is controllable by the controller module based on the detection signal.

14. The system of claim 1, wherein the signal generator module further comprises a pulse generator that is controllable by the controller module based on the control commands to generate pulsed EM radiation from the EM radiation, wherein the EM signal includes the pulsed EM radiation.

15. The system of claim 1, further comprising a fluid feed module having a fluid feed structure in fluid communication with a fluid port for outputting fluid to the electrosurgical instrument, the fluid feed module being controllable by the controller module based on the control commands to supply and control a fluid flow via the fluid feed structure to the fluid port.

16. The system of claim 15, wherein the fluid feed module further comprises a temperature control element coupled to the fluid feed structure and controllable by the controller module based on the control commands to adjust a temperature of the fluid flow in the fluid feed structure.

17. The system of claim 1, further comprising one or more additional signal generator modules operable to generate and control additional EM radiation based on the control commands to form one or more additional EM signals, the or each additional signal generator module generating EM radiation at a different frequency to the signal generator module and to each other additional signal generator module, and wherein the feed structure module has one or more additional signal channels for coupling the or each additional signal generator module to the output port.

18. The system of claim 17, wherein the signal channel and the or each additional signal channel comprise physically separate signal pathways, and wherein the feed structure module comprises a signal combining circuit having one or more inputs, each input connected to a different one of the physically separate signal pathways, the signal combining circuit having an output connected to a common signal pathway for conveying the EM signal and the or each additional EM signal separately or simultaneously along a single channel to the output port.

19. The system of claim 18, wherein the signal combining circuit includes a switching device for connecting one of the signal channel and the or each additional signal channel to the common signal pathway, wherein the switching device is controllable by the controller module based on the control commands.

20. The system of claim 1, further comprising a case for containing multiple modules of the system, the case comprising multiple sockets for receiving the multiple modules.

21. The system of claim 1, further comprising an electrosurgical instrument arranged to deliver EM radiation from a distal end thereof, the electrosurgical instrument having an instrument feed structure for conveying the EM signal to the distal end, the instrument feed structure having an instrument signal channel for connecting the distal end to the output port.

22. A modular electrosurgical system comprising:
   a signal generator module for a modular electrosurgical system, the signal generator module comprising:
      a controller having a wireless communication interface operable to wirelessly communicate with a remote computing device so as to receive data therefrom, the controller being operable to provide control commands based on the received data;
      a signal generator in communication with the controller so as to receive the control commands, the signal generator operable to generate and control electromagnetic (EM) radiation based on the control commands to form an EM signal; and
      a feed structure for conveying the EM signal and having an output port for outputting the EM signal to an electrosurgical instrument, the feed structure having a signal channel for connecting the signal generator to the output port;
   an electrosurgical instrument arranged to deliver EM radiation from a distal end thereof, the electrosurgical instrument having an instrument feed structure for conveying the EM signal to the distal end, the instrument feed structure having an instrument signal channel for coupling the distal end to the output port of the signal generator module; and
   a remote computing device for wirelessly sending data to the wireless communication interface of the signal generator module based on user input data received by the remote computing device.

23. The modular electrosurgical system of claim 22, further comprising:
   a fluid feed module comprising:
      a controller having a wireless communication interface operable to wirelessly communicate with a remote computing device so as to receive data therefrom, the controller being operable to provide control commands based on the received data;
      a fluid feed structure in fluid communication with a fluid port for outputting fluid to an electrosurgical instrument, the fluid feed structure being controllable by the controller based on the control commands to supply and control a fluid flow to the fluid port; and
   a fluid feed structure connected to supply the fluid flow from the fluid port of the fluid feed module to the distal end of the electrosurgical instrument.

24. A signal combining module for a modular electrosurgical system, the signal combining module comprising:
   a controller having a wireless communication interface operable to wirelessly communicate with a remote computing device so as to receive data therefrom, the controller being operable to provide control commands based on the received data;
   a plurality of input ports for receiving a plurality of input electromagnetic (EM) signals;
   an output port for transmitting an output EM signal to an electrosurgical instrument; and
   a feed structure comprising a plurality of separate signal pathways coupled to the plurality of input ports for conveying the plurality of input EM signals to a switching device, the feed structure having a common signal pathway connected to the output port, wherein the switching device is configured to selectively connect one or more of the plurality of separate signal pathways to the common signal pathway based on the control commands.

* * * * *